(12) United States Patent
Wang

(10) Patent No.: US 9,737,243 B2
(45) Date of Patent: Aug. 22, 2017

(54) BLOOD COLLECTION APPARATUS

(71) Applicant: Hsien-Tsung Wang, Taipei (TW)

(72) Inventor: Hsien-Tsung Wang, Taipei (TW)

(*) Notice: Subject to any disclaimer, the term of this patent is extended or adjusted under 35 U.S.C. 154(b) by 54 days.

(21) Appl. No.: 14/334,679

(22) Filed: Jul. 18, 2014

(65) Prior Publication Data

US 2016/0015300 A1     Jan. 21, 2016

(51) Int. Cl.
| | | |
|---|---|---|
| *A61B 5/00* | (2006.01) | |
| *B65D 81/00* | (2006.01) | |
| *A61B 5/15* | (2006.01) | |
| *A61B 5/155* | (2006.01) | |
| *A61B 5/153* | (2006.01) | |
| *A61M 5/32* | (2006.01) | |

(52) U.S. Cl.
CPC .......... *A61B 5/1411* (2013.01); *A61B 5/1427* (2013.01); *A61B 5/1433* (2013.01); *A61B 5/15003* (2013.01); *A61B 5/153* (2013.01); *A61B 5/15074* (2013.01); *A61B 5/150221* (2013.01); *A61B 5/150236* (2013.01); *A61B 5/150244* (2013.01); *A61B 5/150251* (2013.01); *A61B 5/150389* (2013.01); *A61B 5/150503* (2013.01); *A61B 5/150671* (2013.01); *A61B 5/150992* (2013.01); *A61M 5/3216* (2013.01)

(58) Field of Classification Search
CPC ... A61B 5/1411; A61B 5/1427; A61B 5/1433; A61B 5/3216
USPC ........................................................ 600/575
See application file for complete search history.

(56) References Cited

U.S. PATENT DOCUMENTS

| | | | | |
|---|---|---|---|---|
| 3,405,706 A | * | 10/1968 | Cinqualbre ........ | A61B 5/15003 600/575 |
| 3,494,351 A | * | 2/1970 | Horn .................. | A61B 5/15003 600/575 |
| 3,848,581 A | * | 11/1974 | Cinqualbre ........ | A61B 5/15003 600/575 |
| 4,784,157 A | * | 11/1988 | Halls .................. | A61M 5/1408 600/575 |
| 4,999,307 A | * | 3/1991 | Oakley ................ | C12M 33/06 435/309.1 |
| 5,097,842 A | * | 3/1992 | Bonn ................ | A61B 5/150038 600/575 |

(Continued)

FOREIGN PATENT DOCUMENTS

WO       WO 9745055 A1 * 12/1997  ......... A61B 5/15003

*Primary Examiner* — Kristen Matter

(57) ABSTRACT

A blood collection apparatus is provided with a blood collection assembly including a casing tube including a forward nose, a plurality of connectors and a rear flange having a flexible projection, a plunger slidably disposed in the casing tube and including a forward plug and an elongated arm having a plurality of cavities, a blood collection tubes, an adapter assemblies each including a tube body, a first tube extending out of one end and insert into a related connectors of the casing tube, a second tube extending out of the end to insert into one of the blood collection tubes, and a butterfly needle assembly mounted to the nose of the casing tube. A pulling of the plunger moves the plug rearward and pivots the projection to engage in one cavity of the elongated arm and an orifice of the each related connectors is not blocked by the plug so as to flow blood from the tube casing to one of the blood collection tube via one connector and one adapter assembly.

15 Claims, 27 Drawing Sheets

(56) References Cited

U.S. PATENT DOCUMENTS

| | | | |
|---|---|---|---|
| 8,409,508 B2* | 4/2013 | Ririe | B01L 3/502 422/68.1 |
| 2006/0173378 A1* | 8/2006 | Fonss | A61B 5/15003 600/578 |
| 2007/0129618 A1* | 6/2007 | Goldberger | A61B 5/14532 600/345 |

* cited by examiner

BLOOD COLLECTION APPARATUS

BACKGROUND OF THE INVENTION

1. Field of the Invention

The invention relates to blood collection and more particularly to a blood collection apparatus capable of collecting blood in at least one blood collection tube in a single operation.

2. Description of Related Art

Blood collections for sampling are typically performed in blood donation stations, laboratories, or the like. It is often that different blood collection tubes for collecting blood of different volumes are required in a single operation.

However, the conventional blood collection apparatus is capable of collecting blood to store in a single blood collection tube. Unfortunately, a patient may bear a great pain due to a number of pulling of the needle and insertion of the same into the patient if a number of times of blood collection are required to complete the blood collection. Further, a medically employed may be accidentally pricked during the pulls and insertions of the needle, thereby contaminating the employee with microorganisms or blood on the needle is possible. Furthermore, a reuse of the used needle is also made possible.

Thus, the need for improvement still exists.

SUMMARY OF THE INVENTION

It is therefore one object of the invention to provide a blood collection apparatus comprising a plurality of blood collection tubes for collecting blood in a single operation with increased efficiency, simplicity, quickness, time saving, and decreased pain born by a patient.

It is another object of the invention to provide a blood collection apparatus wherein a blood collection tube can be disengaged from the blood collection apparatus even when blood does not completely fill the blood collection tube prior to filling blood in another blood collection tube.

It is still another object of the invention to provide a blood collection apparatus wherein a plunger comprises an elongated arm including a plurality of cavities, wherein a casing tube of a blood collection assembly comprises a rear flange having a flexible projection, and wherein in a blood collection operation a pulling of the plunger and a pivotal movement of the projection engaging in one of the cavities may temporarily fasten the plunger so as to correctly flow blood from the tube casing to one of the blood collection tubes.

It is a further object of the invention to provide an arrangement for a blood collection apparatus wherein after a blood collection operation, a medical employee may pivot a safety device about a pivot member to lockingly conceal a needle in the internally hollowed safety device. This has the benefits of preventing the employee from being accidentally pricked after use, thereby no contaminating the employee with microorganisms or blood on the needle is possible. Further, a reuse of the needle is made impossible.

For achieving above and other objects, in a first aspect of the invention there is provided a blood collection apparatus comprising a blood collection assembly comprising a casing tube including a forward nose, a plurality of connectors and a rear flange having a flexible projection; and a plunger slidably disposed into the casing tube and comprising a forward plug and an elongated arm including a plurality of cavities; a blood collection tubes; a plurality of adapter assemblies each including a tube body, a first tube extending out of one end of the tube body to insert into one of the connectors of the casing tube, and a second tube extending out of another end of the tube body to insert into one of the blood collection tubes; and a butterfly needle assembly mounted to the nose of the casing tube; wherein in a blood collection operation of pulling of the plunger moves the plug rearward and pivots the projection to engage in one of the cavities of the elongated arm and an orifice of each said related connector is not blocked by the plug so as to flow blood from the casing tube to one of the blood collection tubes via one of the connectors and one of the adapter assemblies.

According to an embodiment of the present invention, the nose is formed on a forward end of the casing tube and is inserted into a rear housing member of a tubing member.

According to an embodiment of the present invention, the flexible projection of the rear flange is configured to engage within one of the cavities on the elongated arm.

Preferably, the butterfly needle assembly comprises two wings and a tunnel interconnecting the wings.

Preferably, the butterfly needle assembly further comprises a needle housing, a forward needle mounted to the needle housing, a tubing member having a forward end fastened in the needle housing, and a housing member mounted to a rear end of the tubing member.

Preferably, there is further comprised of a projecting pivot member formed on the butterfly needle assembly, and a safety device including an internally hollowed body having a through hole at one end, the through hole being pivotably put on the pivot member so that the safety device is configured to pivot about the pivot member.

Preferably, the safety device further comprises an internal space defined by the internally hollowed body and open to one side, and at least one blocking member disposed in the internal space wherein after the blood collection operation, a pivotal movement of the safety device about the pivot member passes the needle through both one side of the internal spaced and the at least one blocking member to be lockingly concealed in the internal space.

Preferably, the safety device further comprises an internal space defined by the internally hollowed body and open to a bottom, and at least one blocking member disposed in the internal space wherein after the blood collection operation, a pivotal movement of the safety device about the pivot member passes the needle through both the bottom of the internal spaced and the at least one blocking member to be lockingly concealed in the internal space.

Preferably, the butterfly needle assembly further comprises a needle housing integrally formed with the tunnel.

Preferably, the butterfly needle assembly further comprises a retaining ring securely put on the needle housing, and a projecting pivot member formed on the retaining ring wherein the through hole is pivotably put on the pivot member so that the safety device is configured to pivot about the pivot member.

Preferably, the safety device further comprises spaced first and second protuberances formed proximate to the through hole, wherein the pivot member comprises a peg formed on an outer surface, and wherein before the blood collection operation, the peg engages the second protuberance, and after the blood collection operation, the peg is stopped by the first protuberance.

In a second aspect of the invention there is provided an arrangement for a blood collection apparatus comprising a butterfly needle assembly comprising a needle housing, a pivot member formed on an outer surface of the needle housing, and a forward needle mounted to the needle housing; and a safety device comprising an internally hollowed body including a through hole at one end, the through hole being pivotably put on the pivot member so that the safety device is configured to pivot about the pivot member.

Preferably, the butterfly needle assembly further comprises two wings and a tunnel interconnecting the wings, and wherein the needle housing is integrally formed with the tunnel.

In a third aspect of the invention there is provided an arrangement for a blood collection apparatus comprising a butterfly needle assembly comprising a needle housing, a forward needle mounted to the needle housing, a retaining ring securely put on the needle housing, and a projecting pivot member formed on the retaining ring; a safety device comprising an internally hollowed body including a through hole at one end, the through hole being pivotably put on the pivot member so that the safety device is configured to pivot about the pivot member.

The above and other objects, features and advantages of the invention will become apparent from the following detailed description taken with the accompanying drawings.

DETAILED DESCRIPTION OF THE INVENTION

Figure 1:
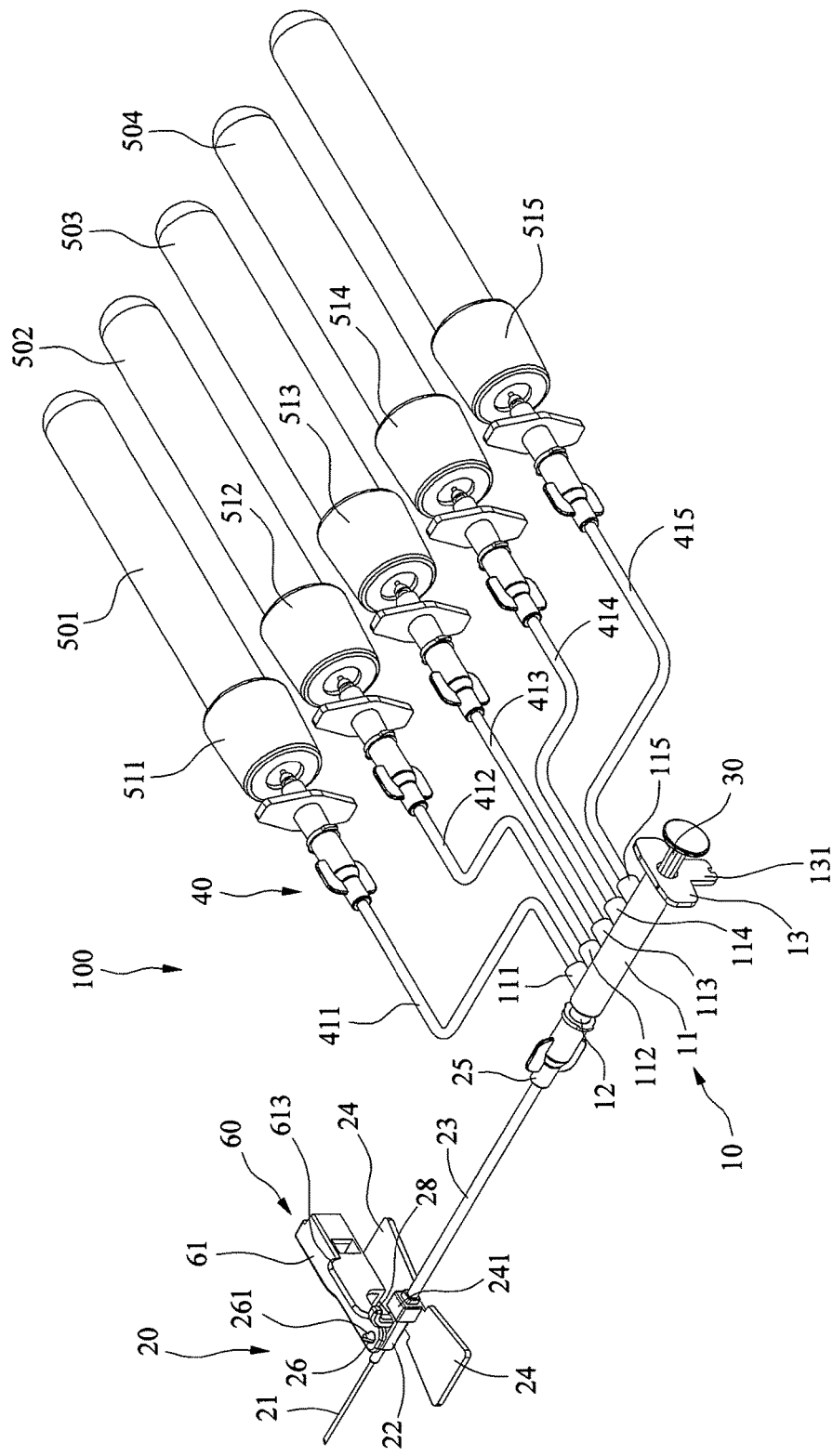
FIG. 1 is a perspective view of a blood collection apparatus according to a first preferred embodiment of the invention.
Figure 2:
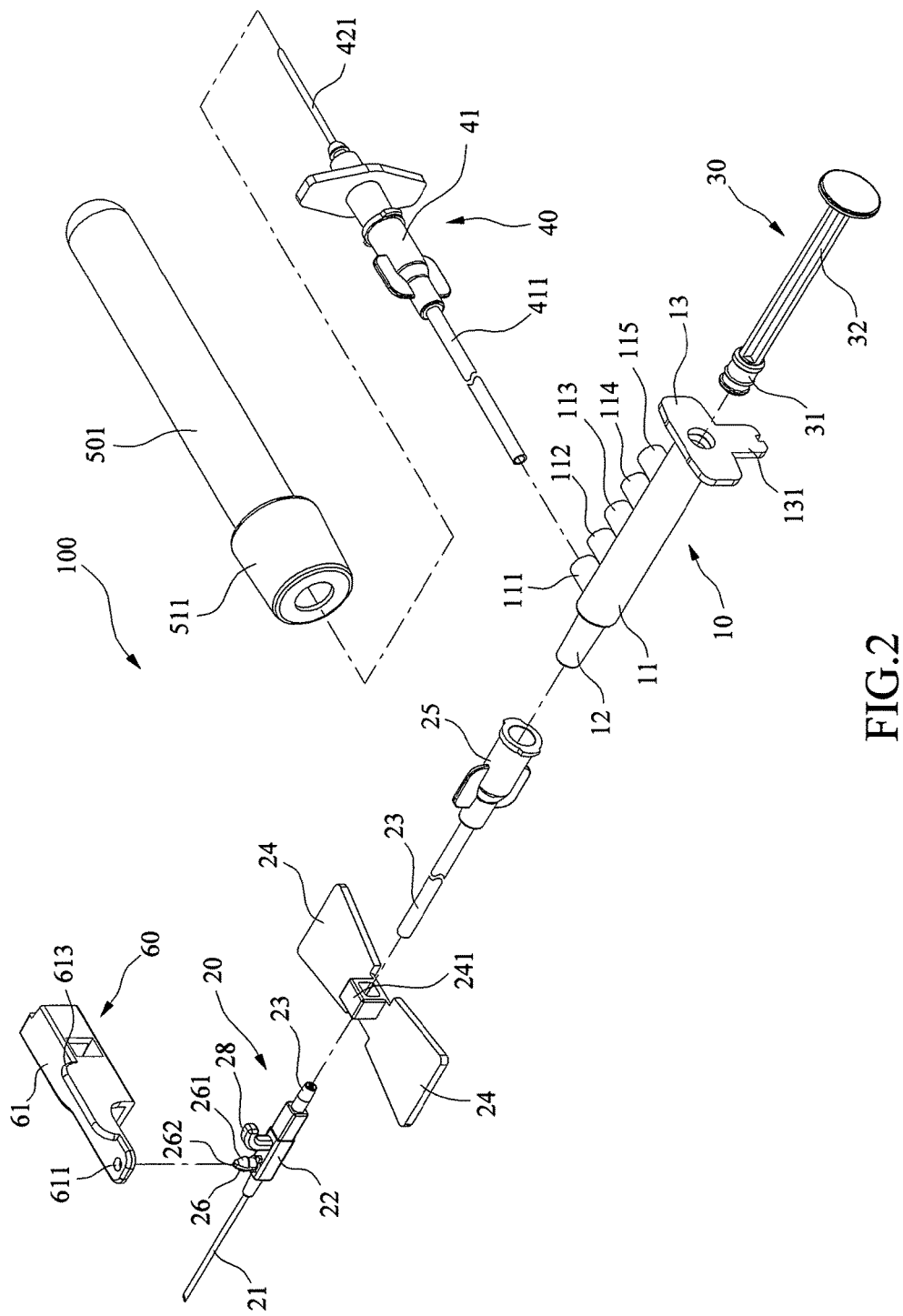
FIG. 2 is an exploded view of the blood collection apparatus of FIG. 1.
Figure 3:
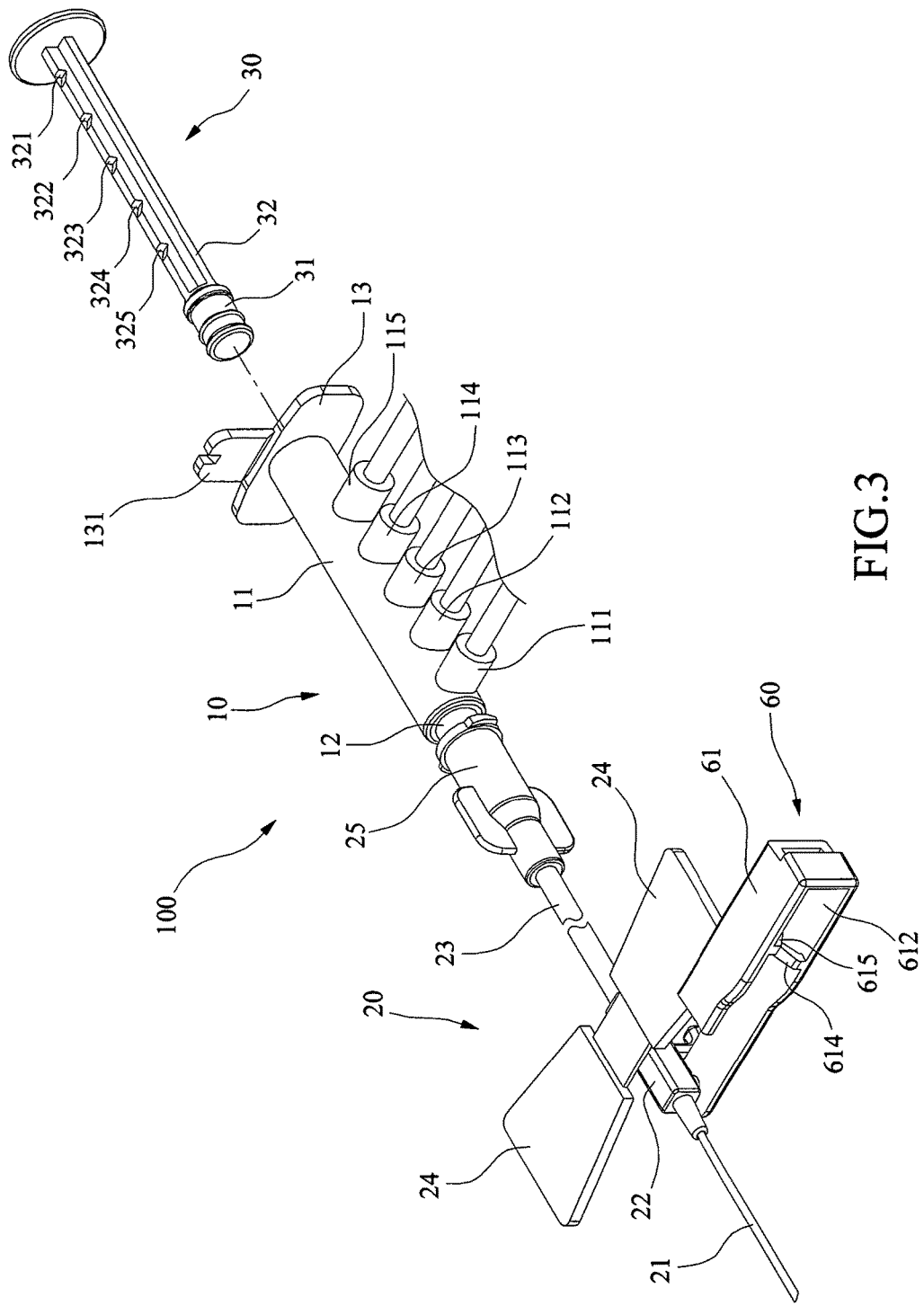
FIG. 3 is an exploded perspective view of some components shown in FIG. 1.

Referring to FIGS. 1, 2, 3, 4, 8, 10 and 11, a blood collection apparatus 100 in accordance with a first preferred embodiment of the invention comprises a blood collection assembly 10, a butterfly needle assembly 20, a plunger 30, five adapter assemblies 40, five blood collection tubes 501, 502, 503, 504 and 505, and a safety device 60.

For example, one adapter assembly 40 includes a body 41, a first tube 411 extending out of one end, and a second tube 421 extending out of the other end to insert into the blood collection tube 501. The casing tube 11 includes five aligned first, second, third, fourth, and fifth connectors 111, 112, 113, 114 and 115 on an outer surface. The first, second, third, fourth, and fifth connectors 111, 112, 113, 114 and 115 are connected to the first tubes 411, 412, 413, 414 and 415 respectively. A nose 12 is formed on a forward end of the casing tube 11 and is inserted into a rear housing member 25 of a tubing member 23. A flange 13 is formed on a rear end of the casing tube 11 and has a flexible projection 131 which is configured to engage within one of first, second, third, fourth, and fifth cavities 321, 322, 323, 324, and 325.

The butterfly needle assembly 20 further includes a needle housing 22, a forward needle 21 mounted to the needle housing 22, two wings 24, a tunnel 241 interconnecting the wings 24 to allow a forward end of the tubing member 23 to dispose therein and secure to the needle housing 22, a projecting pivot 26 having a conic head 261 and a slit 262 through the head 261, and a bent handle 28 besides the pivot 26.

The plunger 30 includes a front plug 31 and an elongated arm 32. The plunger 30 is snugly, slidably disposed in the casing tube 11 to prevent blood in the casing tube 11 from being leaked. The arm 32 has the first, second, third, fourth, and fifth cavities 321, 322, 323, 324, and 325 formed thereon. The first, second, third, fourth, and fifth cavities 321, 322, 323, 324, and 325 correspond to the first, second, third, fourth, and fifth connectors 111, 112, 113, 114 and 115 respectively.

The adapter assembly 40 includes a first tube 411, 412, 413, 414 or 415 which is connected to one of the first, second, third, fourth, and fifth connectors 111, 112, 113, 114 and 115, and a second tube (e.g., second tube 421) inserted through an adapter 511 at one end of the blood collection tube 501 to dispose in the blood collection tube 501 for flowing collected blood to the blood collection tube 501 for storage. It is noted that the blood collection tube 502 has an adapter 512, the blood collection tube 503 has an adapter 513, the blood collection tube 504 has an adapter 514, and the blood collection tube 505 has an adapter 515 respectively.

The safety device 60 includes an internally hollowed body 61 having an internal space 612 defined therein and a through hole 611 at one end, the through hole 611 pivotably put on a portion between the head 261 and the needle housing 22, a projecting edge 613 for facilitating pivotal movement of the safety device 60 by hand, and parallel first and second blocking members 614, 615 provided in the internal space 612 and the first blocking member 614 being at an angle with respect to the second blocking member 615.

Figure 8:
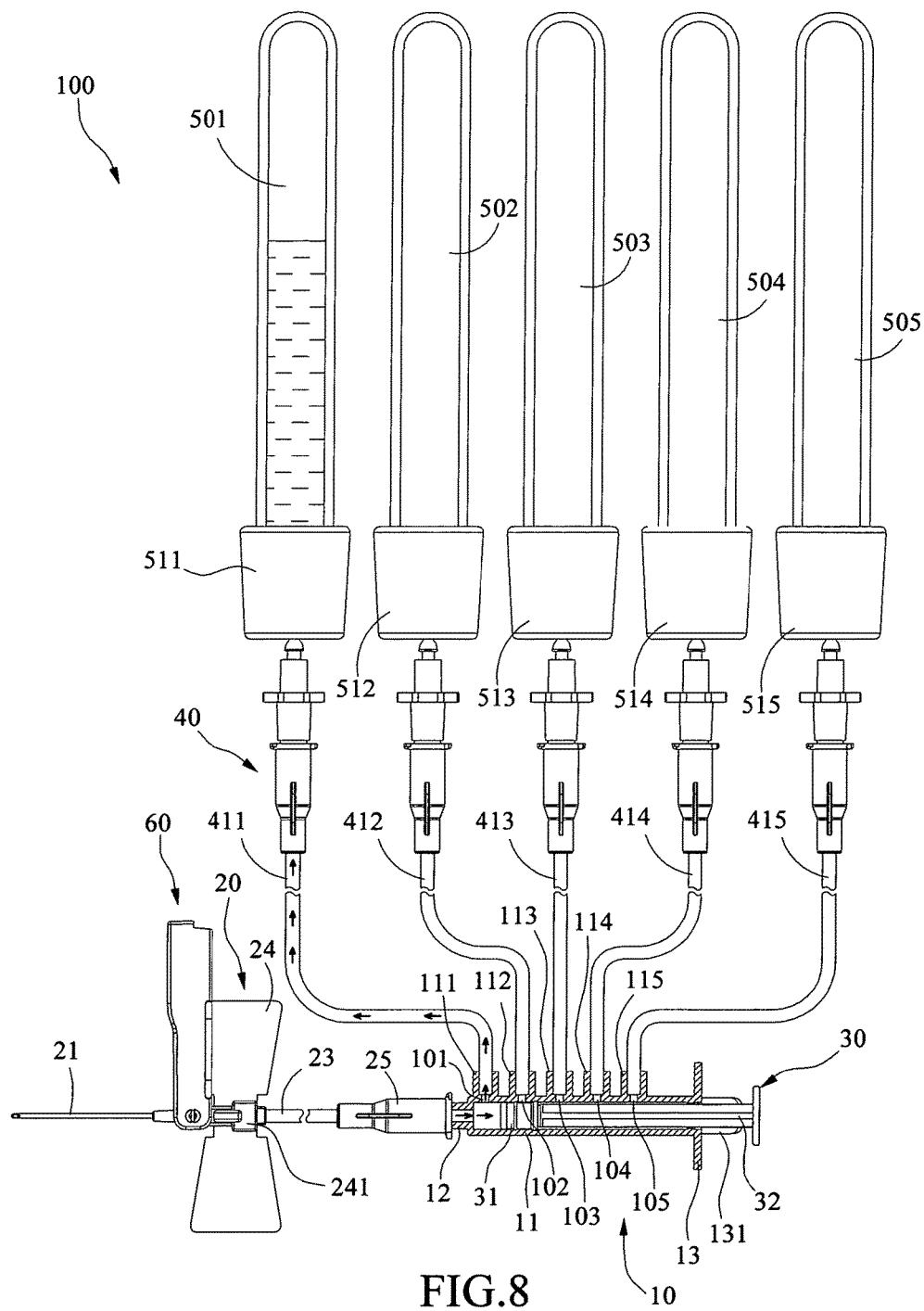
FIG. 8 is a top view of FIG. 1 in part section showing a first position of blood collection.
Figure 9:
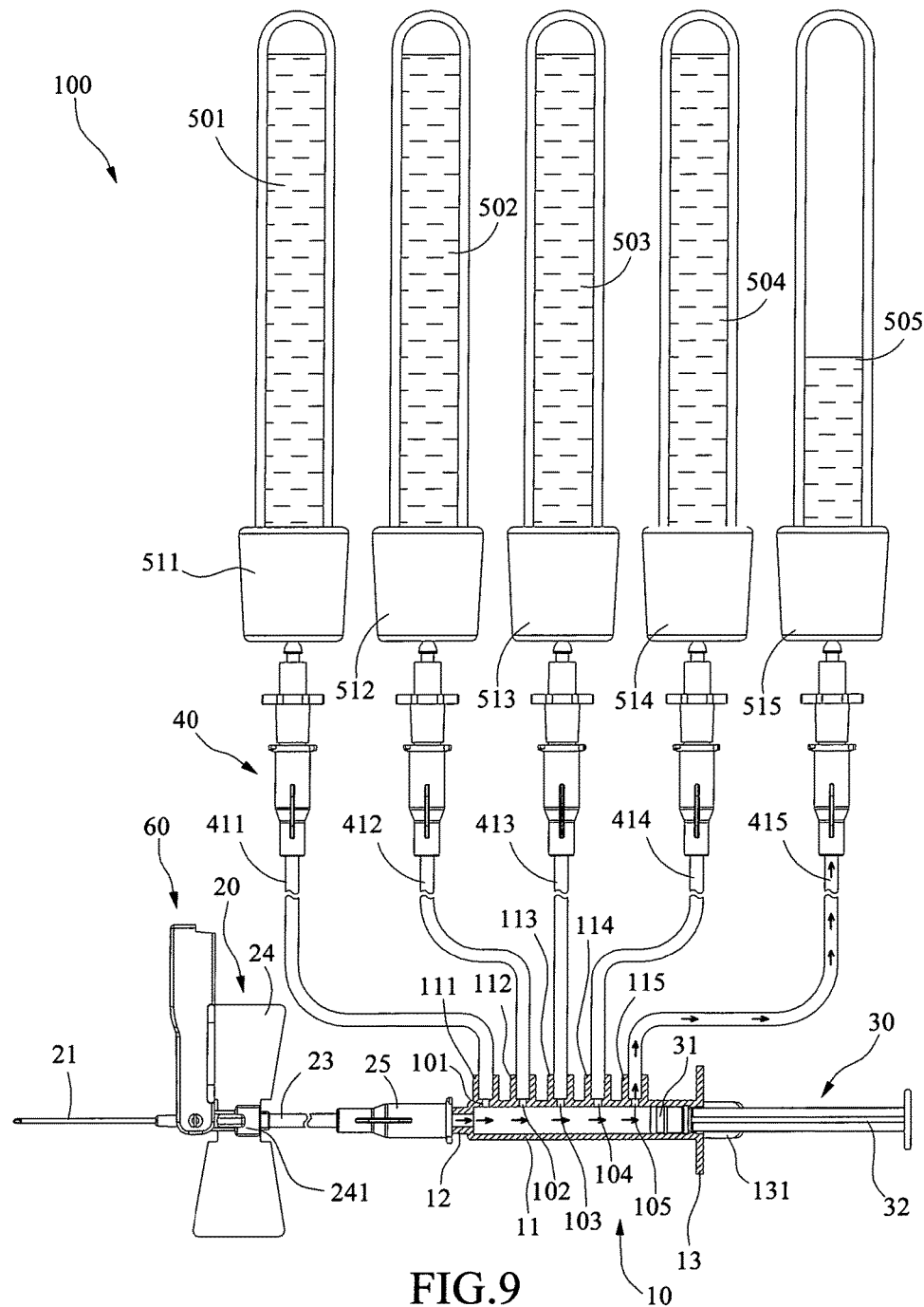
FIG. 9 is a view similar to FIG. 8 showing the fifth position of blood collection.
Figure 10:
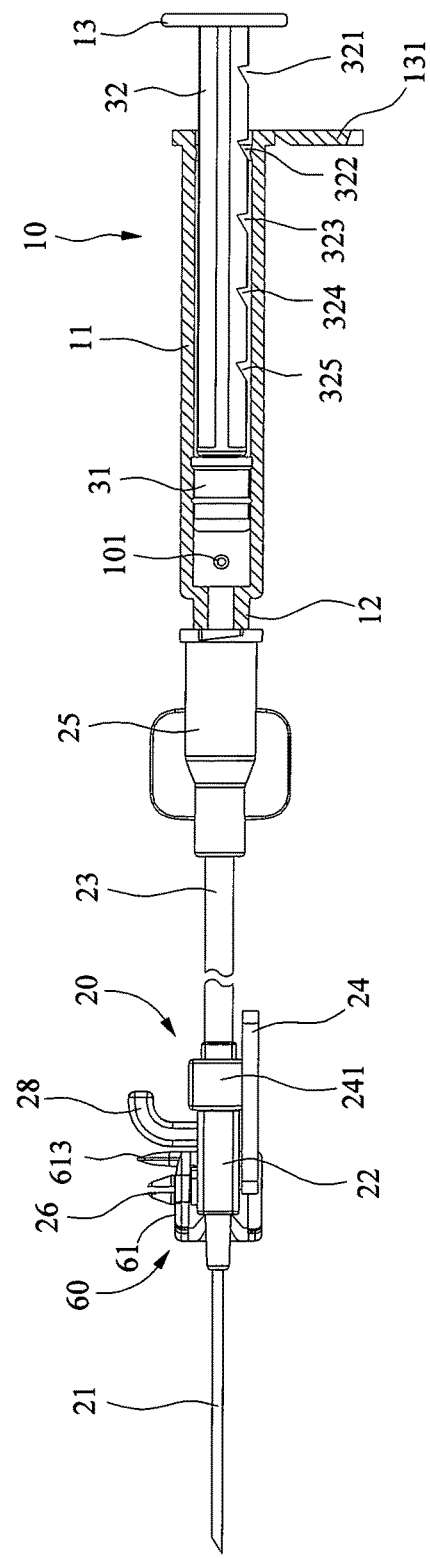
FIG. 10 is a longitudinal sectional view of the blood collection assembly shown in FIG. 1 with no blood being collected.
Figures 11, 12, 13:
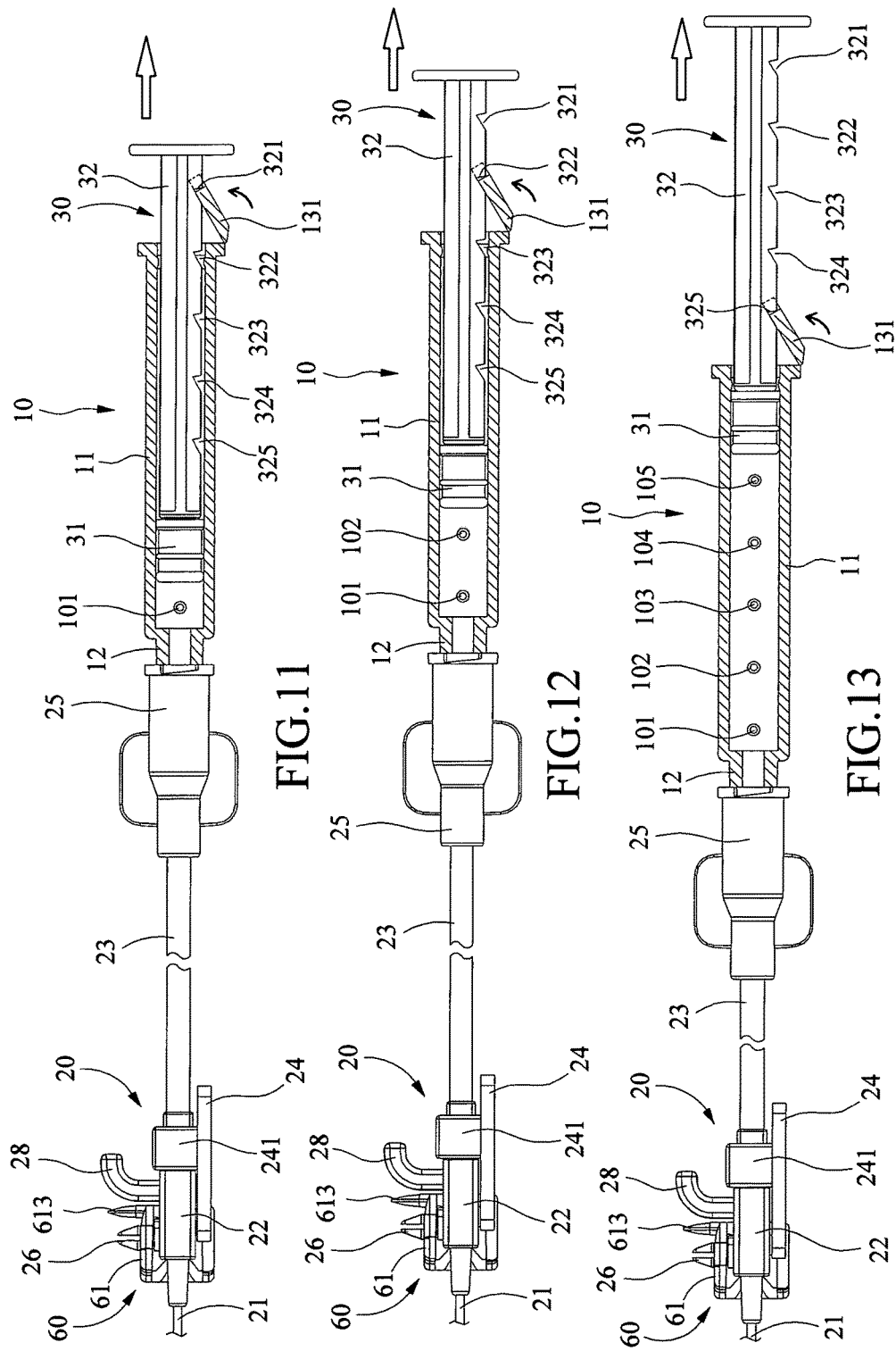
FIG. 11 is a view similar to FIG. 10 showing the projection is engaged within a first cavity in the first position of blood collection.
FIG. 12 is a view similar to FIG. 11 showing the projection is engaged within a second cavity in the second position of blood collection.
FIG. 13 is a view similar to FIG. 11 showing the projection is engaged within a fifth cavity in the fifth position of blood collection.
Figure 14:
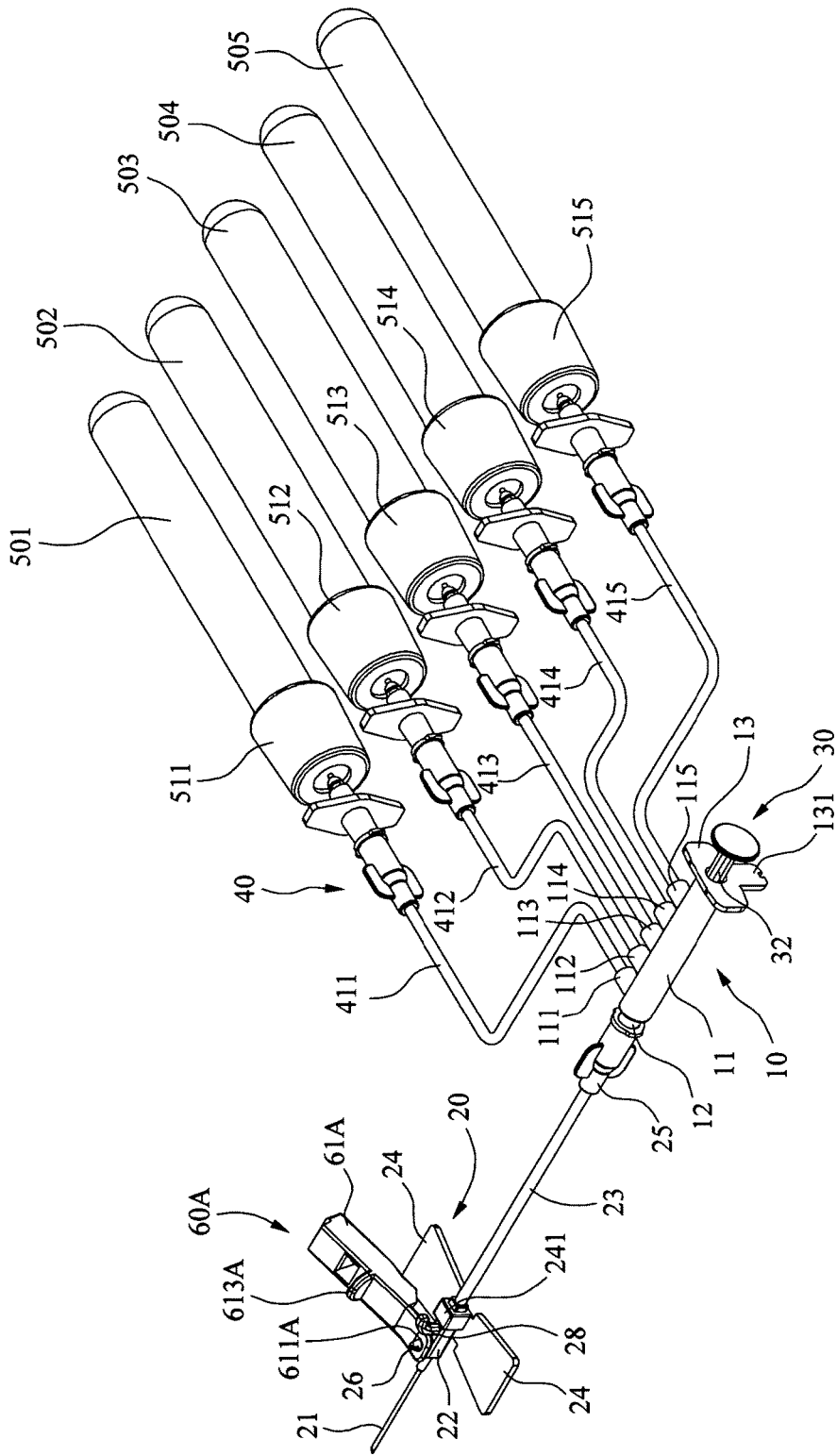
FIG. 14 is a perspective view of a blood collection apparatus according to a second preferred embodiment of the invention.
Figure 15:
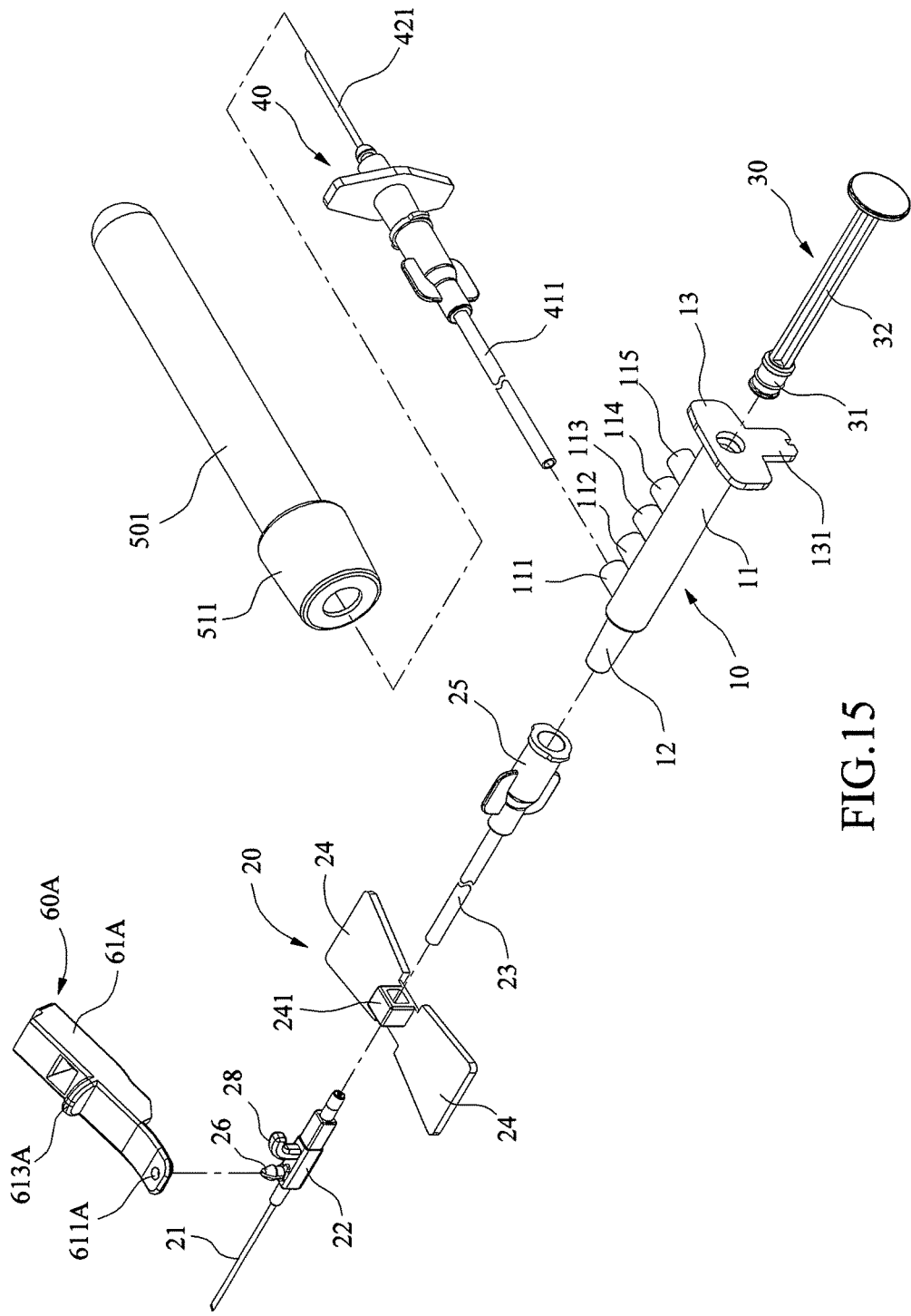
FIG. 15 is an exploded view of the blood collection apparatus of FIG. 14.
Figure 16:
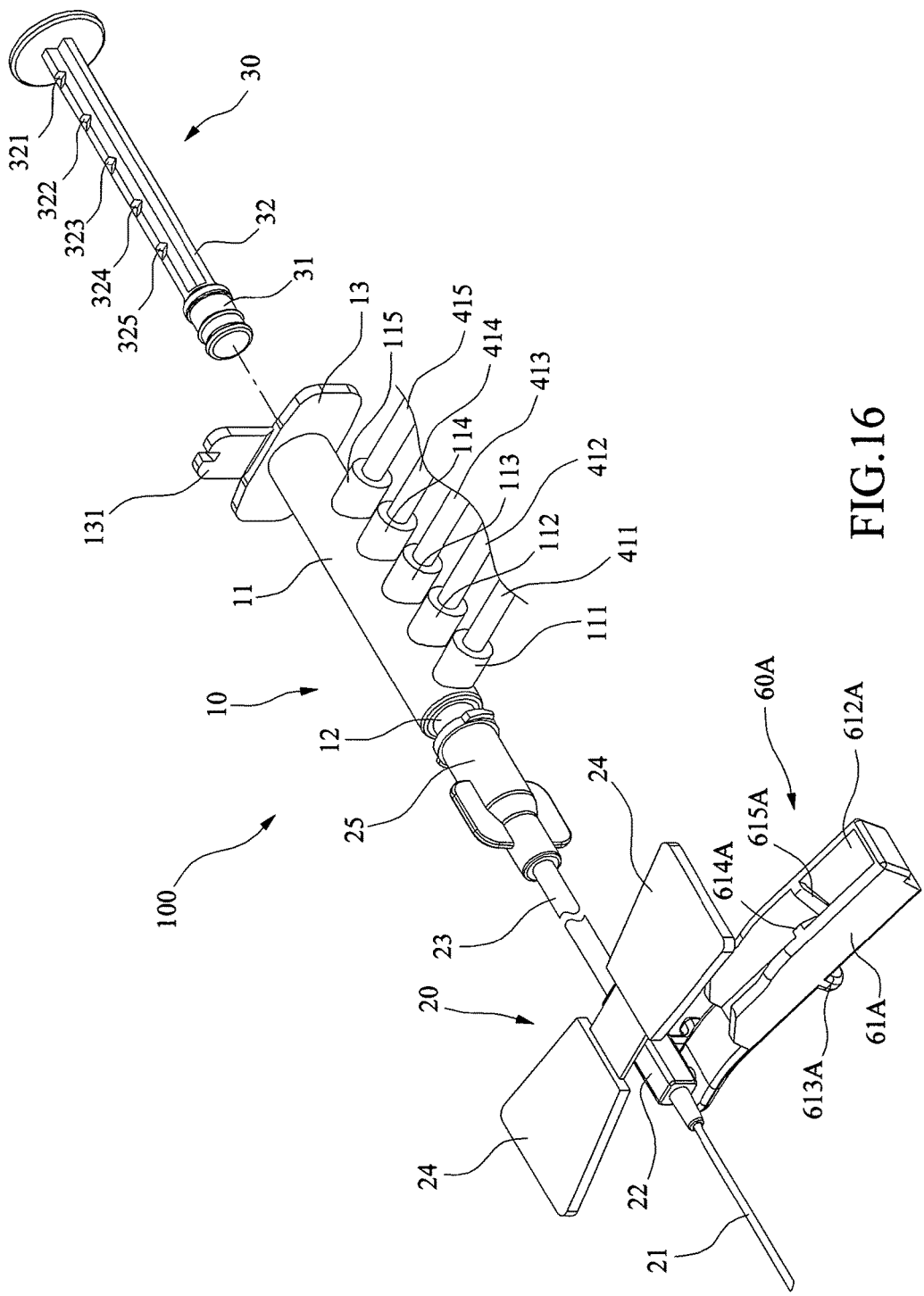
FIG. 16 is an exploded perspective view of some components shown in FIG. 14.
Figure 17:
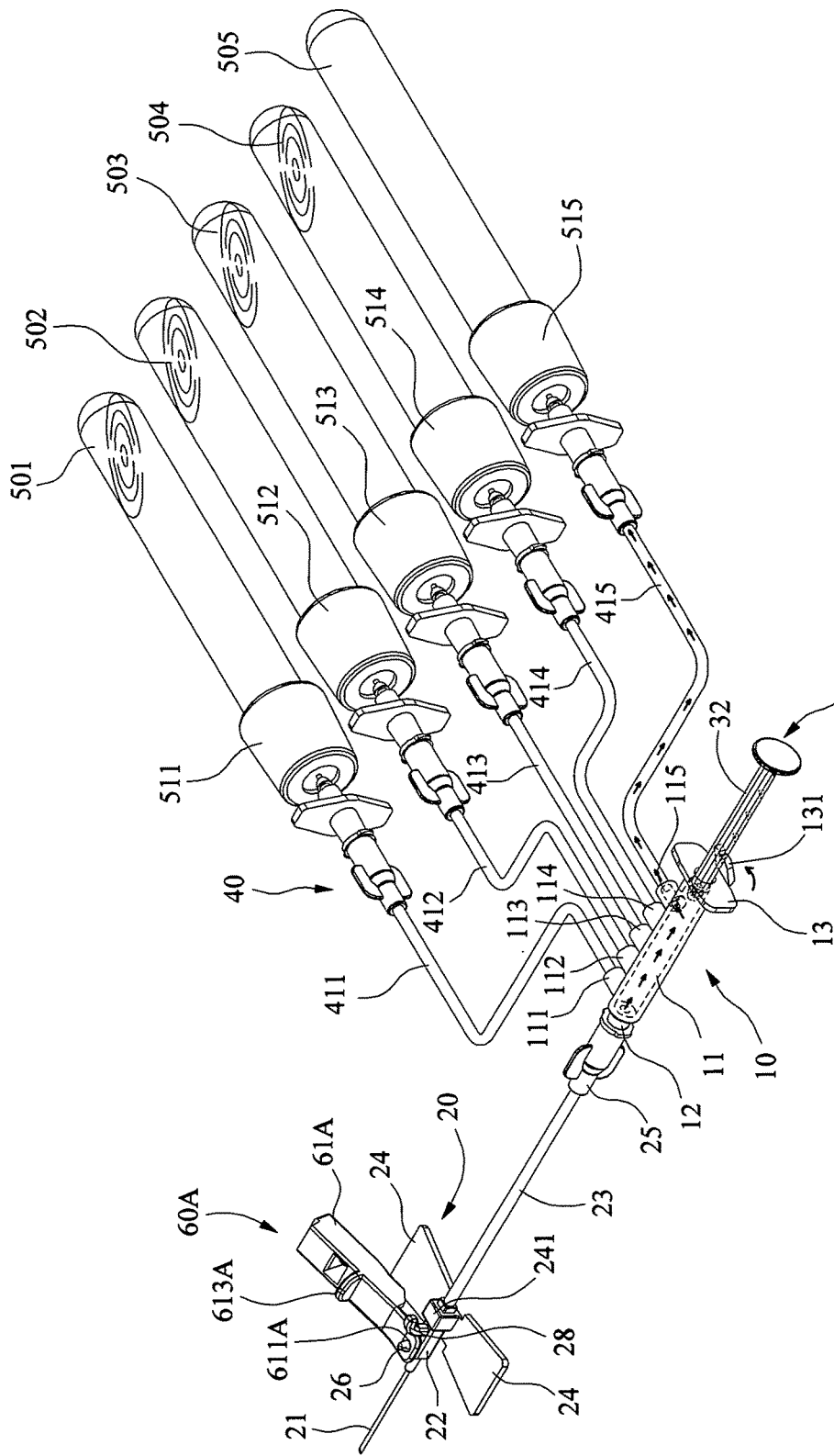
FIG. 17 is a view similar to FIG. 14 showing a ready to use position.
Figure 18:
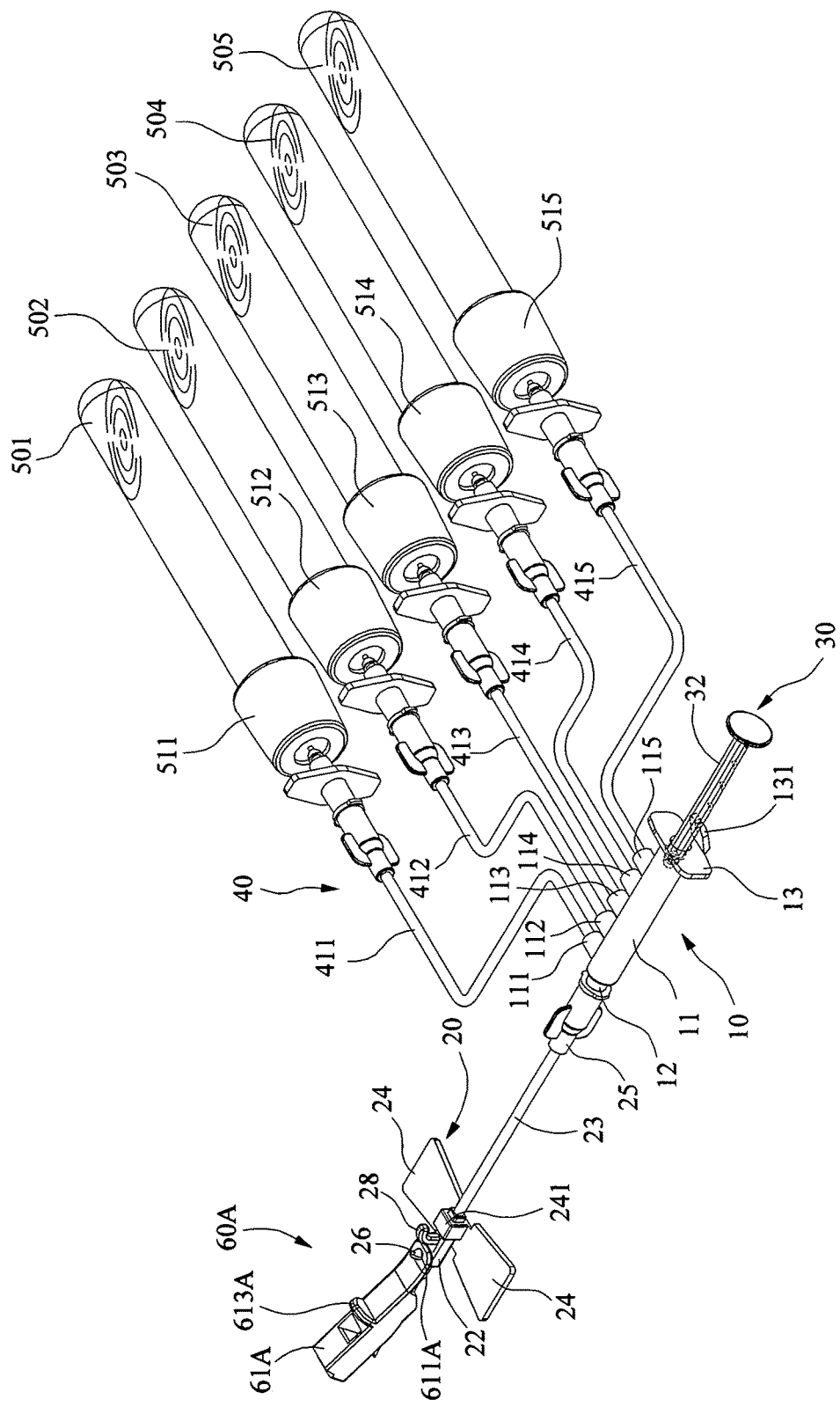
FIG. 18 is a view similar to FIG. 17 showing a use position.
Figure 19A:
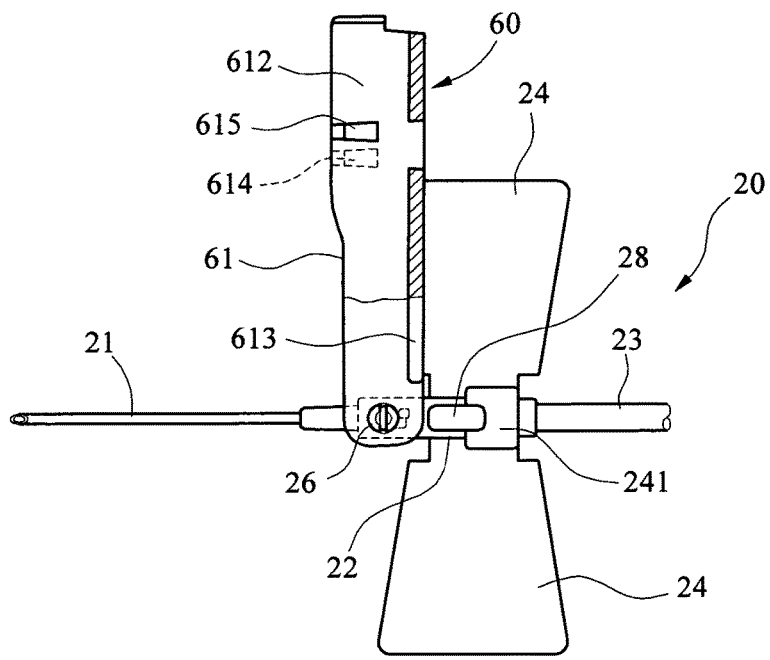
FIG. 19A is a top view in part section of the safety device of FIG. 1 in a position ready to use.
Figure 19B:
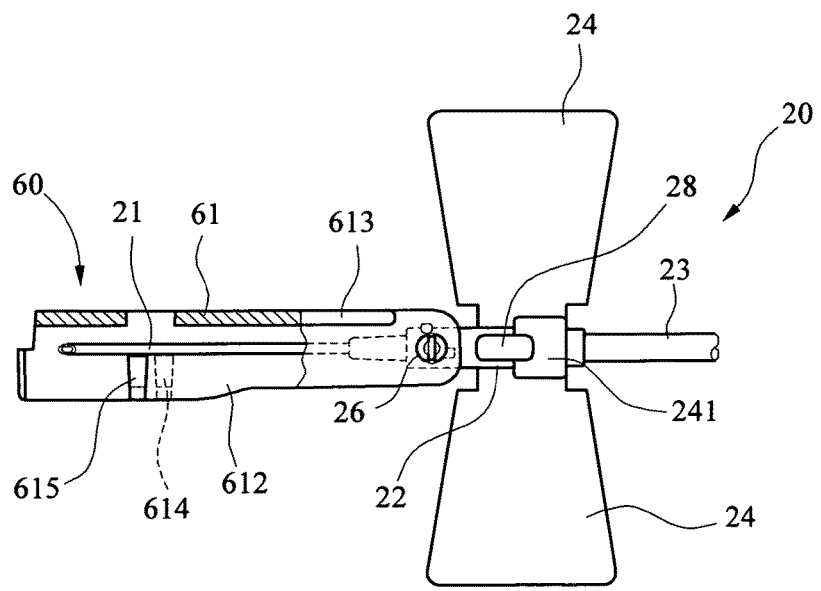
FIG. 19B is view similar to FIG. 19A showing a use position of the safety device.
Figure 20A:
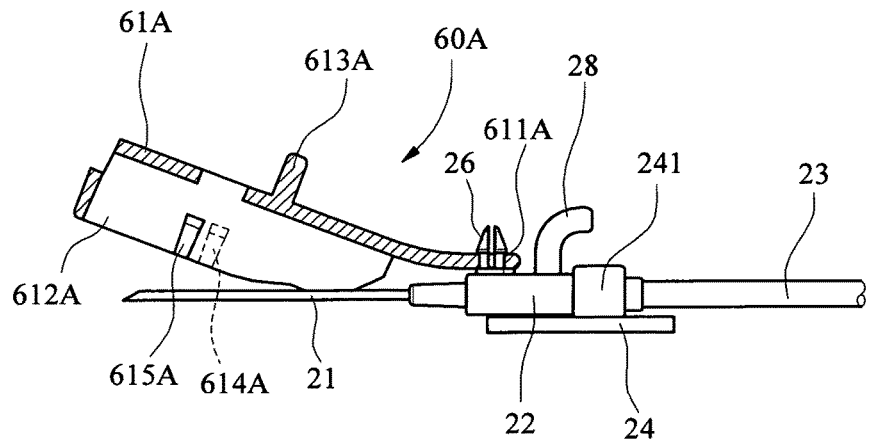
FIG. 20A is a side elevation in part section of the safety device of FIG. 14 showing a position ready to use.
Figure 20B:
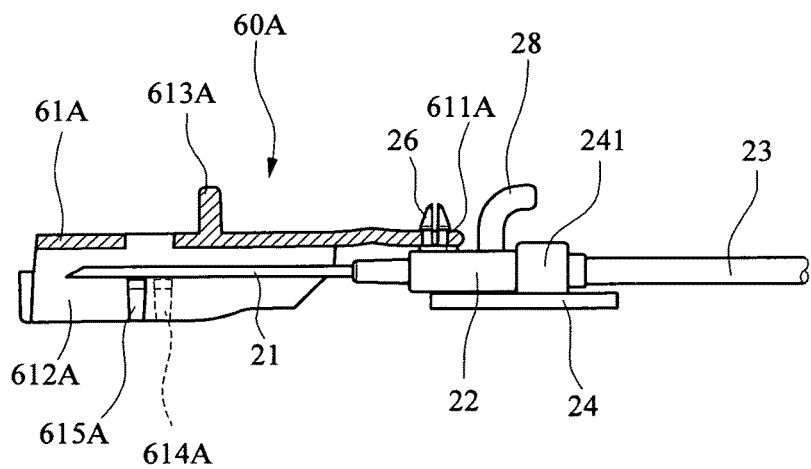
FIG. 20B is view similar to FIG. 20A showing a use position of the safety device.

In a blood collection operation, a medical employee may pull the plunger 30 rearward to move the plug 31 and pivot the projection 131 until the projection 131 is engaged within the first cavity 321 and a first orifice 101 is not blocked by the plug 31 (see FIGS. 8 and 11). Next, blood flows from the needle 21 to the casing tube 11 via the tubing member 23. Finally the blood flows into the first blood collection tube 501 via the first orifice 101, the first connector 111, the first tube 411, and the second tube 421.

Figure 4:
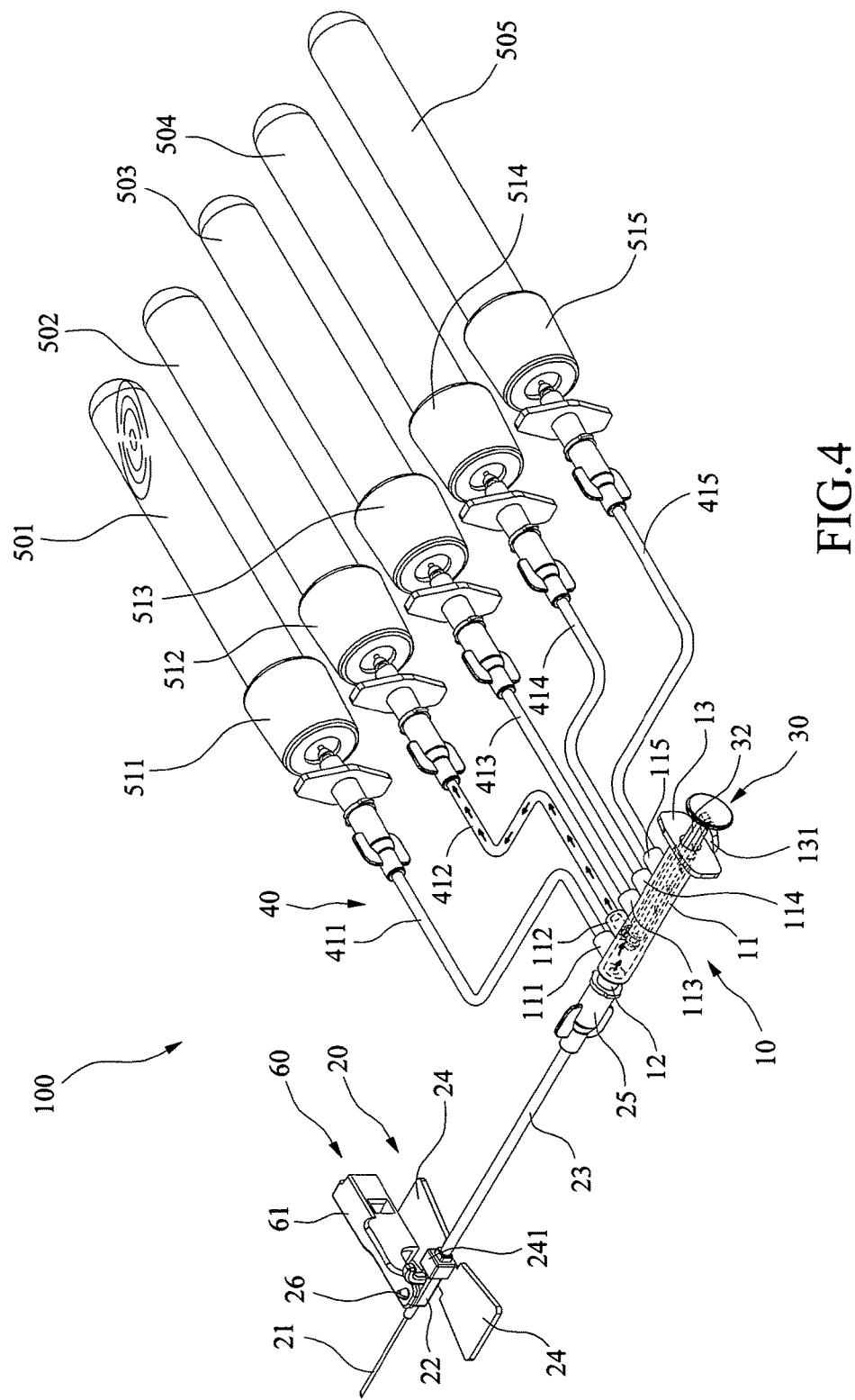
FIG. 4 is a view similar to FIG. 1 showing a second position of blood collection.

Likewise, for collecting blood in the second blood collection tube 502, a medical employee may pull the plunger 30 rearward to move the plug 31 and pivot the projection 131 until the projection 131 is engaged within the second cavity 322 and a second orifice 102 is not blocked by the plug 31 (see FIGS. 4 and 12). Next, blood flows from the needle 21 to the casing tube 11 via the tubing member 23. Finally the blood flows into the second blood collection tube 502 via the second orifice 102, the second connector 112, the first tube 412, and the second tube.

Figure 5:
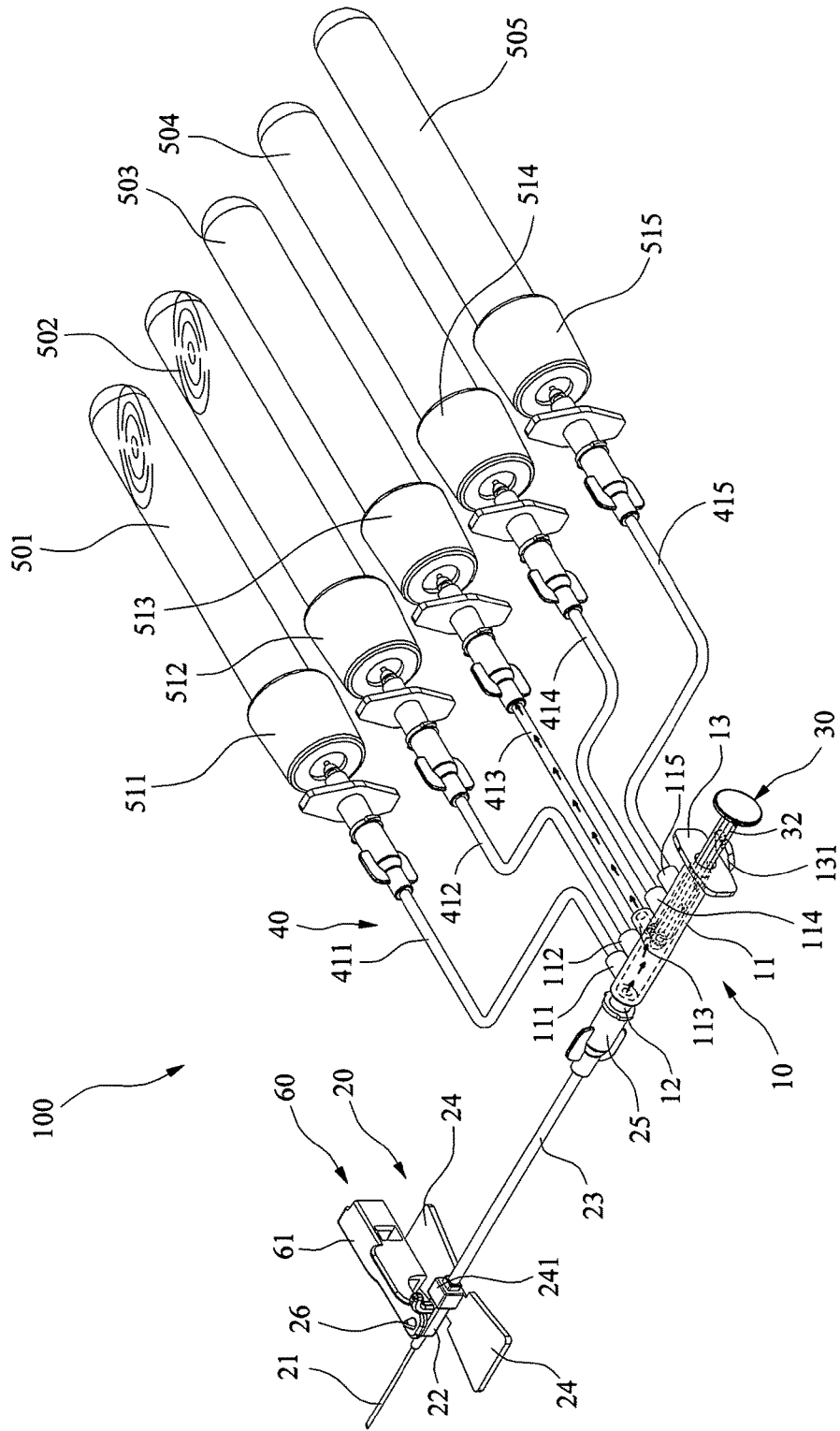
FIG. 5 is a view similar to FIG. 1 showing a third position of blood collection.
Figure 6:
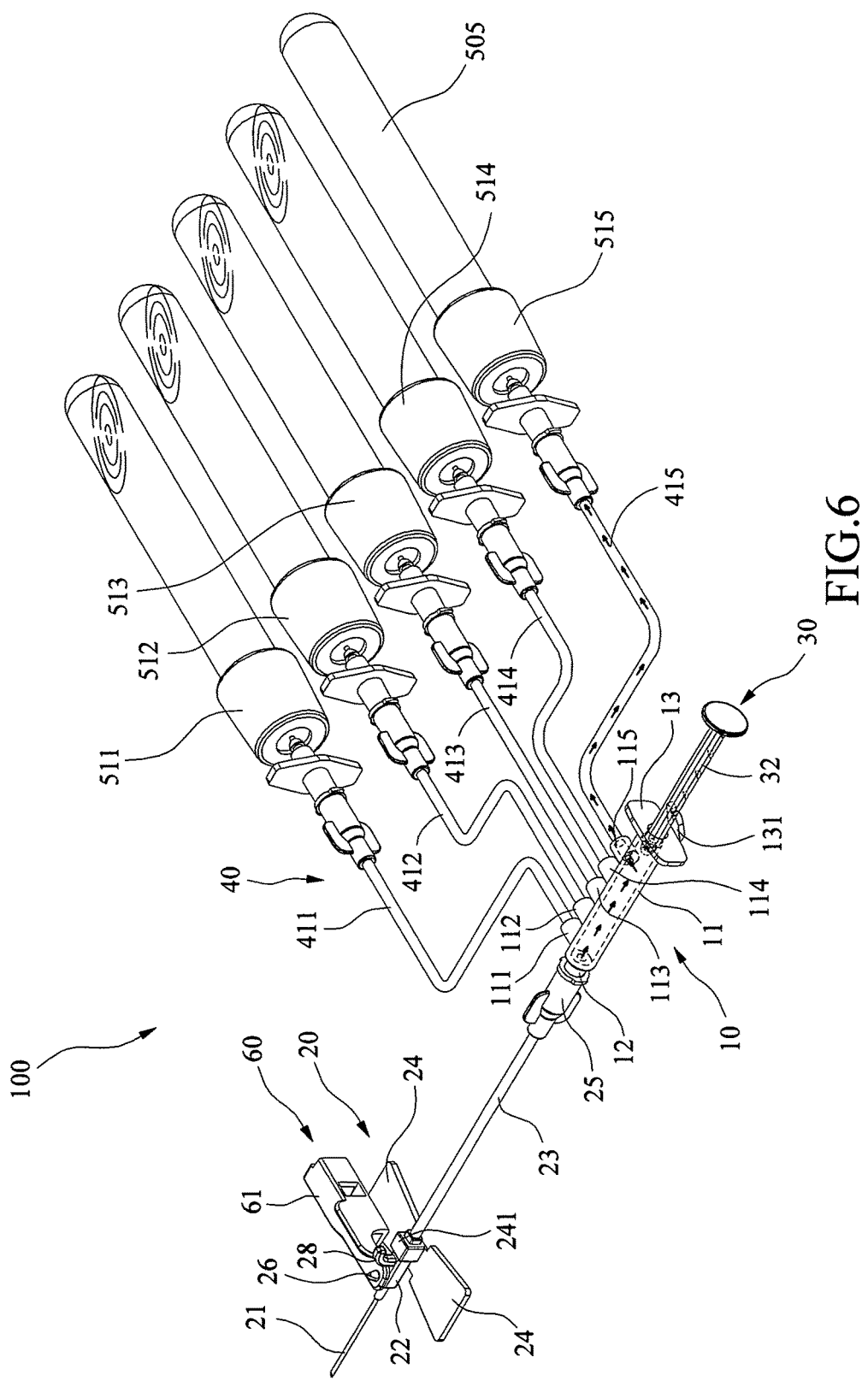
FIG. 6 is a view similar to FIG. 1 showing a fifth position of blood collection.
Figure 7:
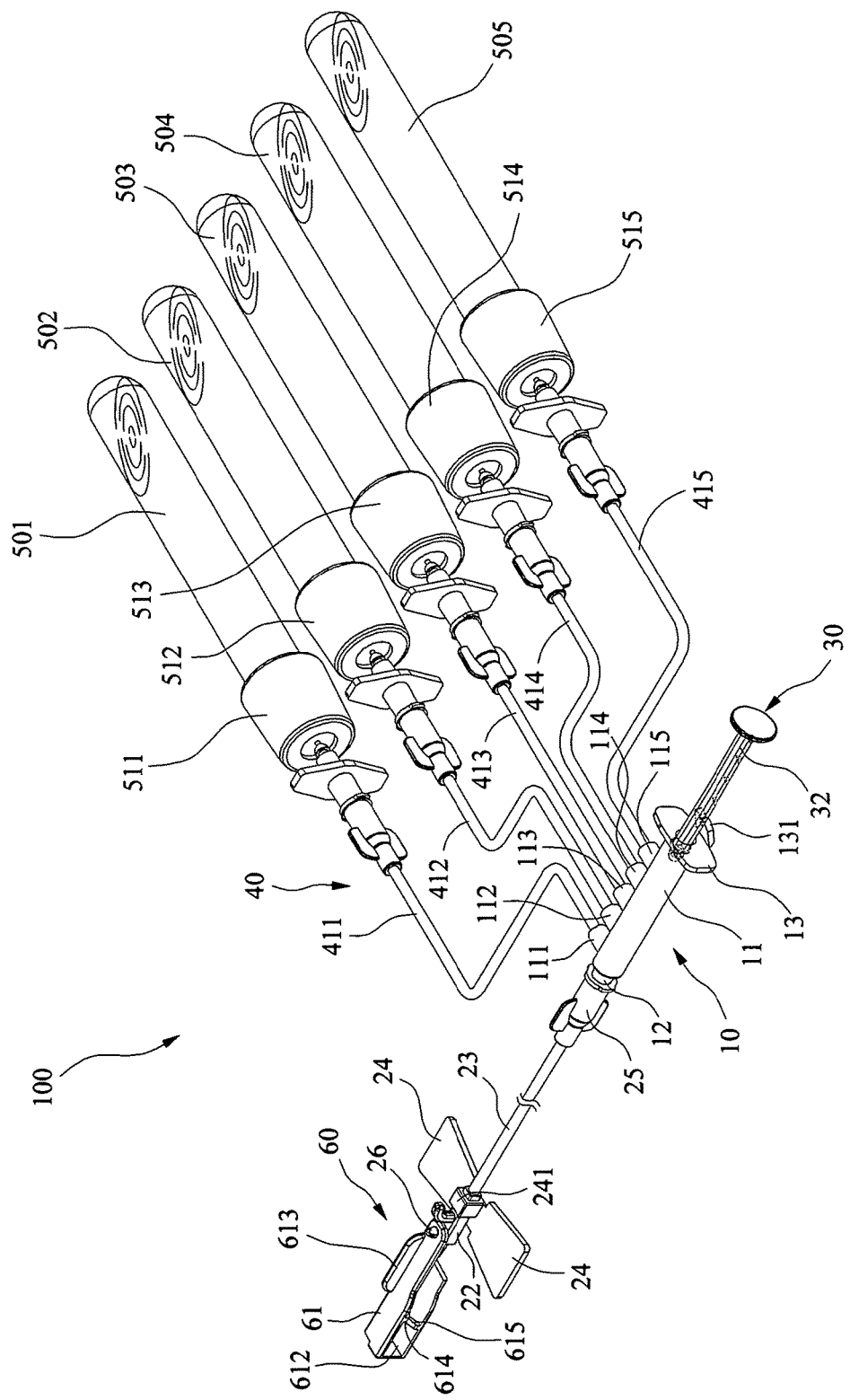
FIG. 7 is a view similar to FIG. 1 showing an operation of the safety device.

Likewise, for collecting blood in the third blood collection tube 503, a medical employee may pull the plunger 30 rearward to move the plug 31 and pivot the projection 131 until the projection 131 is engaged within the third cavity 323 and a third orifice 103 is not blocked by the plug 31 (see FIG. 5). Next, blood flows from the needle 21 to the casing tube 11 via the tubing member 23. Finally the blood flows into the third blood collection tube 503 via the third orifice 103, the third connector 113, the first tube 413, and the second tube.

Operation for collecting blood in the fourth blood collection tube 504 is similar to the above description regarding the third blood collection tube 503. Likewise, for collecting blood in the fifth blood collection tube 505, a medical employee may pull the plunger 30 rearward to move the plug 31 and pivot the projection 131 until the projection 131 is engaged within the fifth cavity 325 and a fifth orifice 105 is not blocked by the plug 31 (see FIGS. 6, 7, 9 and 13). Next, blood flows from the needle 21 to the casing tube 11 via the tubing member 23. Finally the blood flows into the fifth blood collection tube 505 via the fifth orifice 105, the fifth connector 115, the first tube 415, and the second tube. As a result, blood can be collected in a plurality of blood collection tubes in a single pulling of the plunger 30. It is noted that blood can be collected in at least one blood collection tube as shown or more than five blood collection tubes in other embodiments if such need arises.

After the blood collection operation, a medical employee may pivot the safety device 60 about the pivot 26 about 90 degrees by holding and pivoting the projecting edge 613 to cause the needle 21 to pass through a gap between the first blocking member 614 and the second blocking member 615 to be lockingly concealed in the internal space 612 (see FIGS. 7, 19A, 19B, 23 and 24). This has the benefits of preventing the employee from being accidentally pricked after use, thereby contaminating the employee with microorganisms or blood on the needle 21. Further, a reuse of the needle 21 is made impossible.

Referring to FIGS. 14, 15, 16, 17, 18, 20A and 20B, a blood collection apparatus incorporating a second preferred embodiment of a safety device 60A in accordance with the invention is shown. The characteristics of the second preferred embodiment are described below.

The safety device 60A includes an internally hollowed body 61A having an internal space 612A defined therein and a through hole 611A at one end, the through hole 611A pivotably put on a portion between the pivot 26, a protrusion 613A on a top for facilitating pivotal movement of the safety device 60A by hand, and parallel first and second blocking members 614A, 615A provided in the internal space 612A and the first blocking member 614A being at an angle with respect to the second blocking member 615A. After the blood collection operation, a medical employee may pivot the safety device 60A about the pivot 26 about 90 degrees by holding and pivoting the protrusion 613A to cause the needle 21 to pass through a gap between the first blocking member 614A and the second blocking member 615A to be lockingly concealed in the internal space 612A. This has the benefits of preventing the employee from being accidentally pricked after use, thereby contaminating the employee with microorganisms or blood on the needle 21. Further, a reuse of the needle 21 is made impossible.

Figure 21:
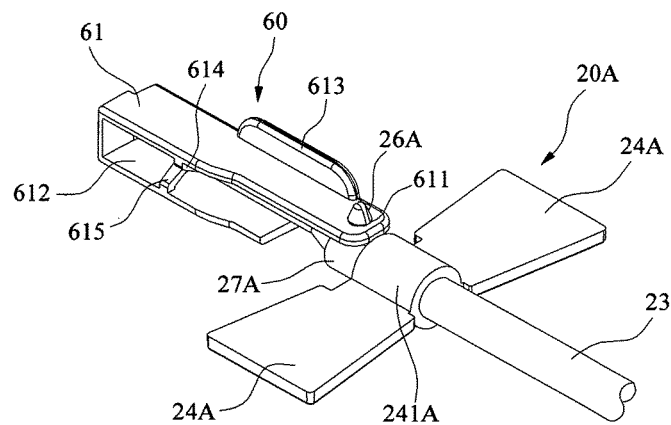
FIG. 21 is a perspective view of a safety device and a butterfly needle assembly according to a third preferred embodiment of the invention.
Figure 22:
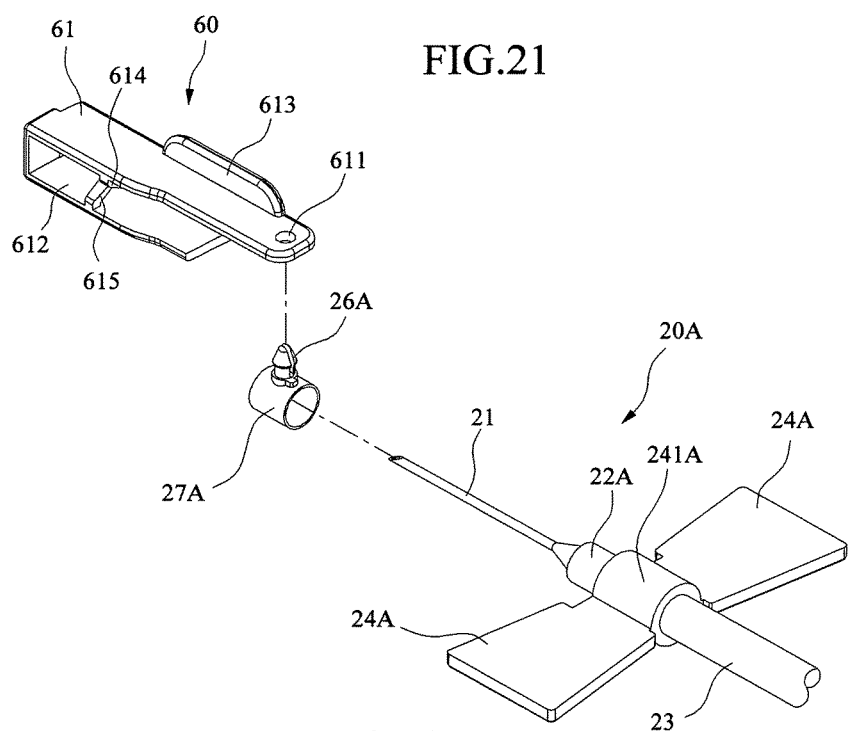
FIG. 22 is an exploded view of the safety device and the butterfly needle assembly shown in FIG. 21.
Figure 23:
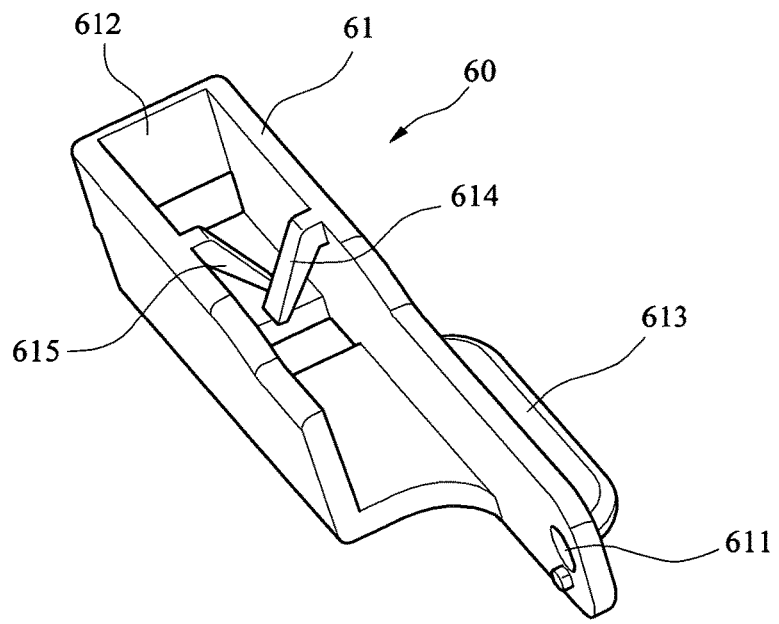
FIG. 23 is a perspective view of the safety device shown in FIG. 19A.
Figure 24:
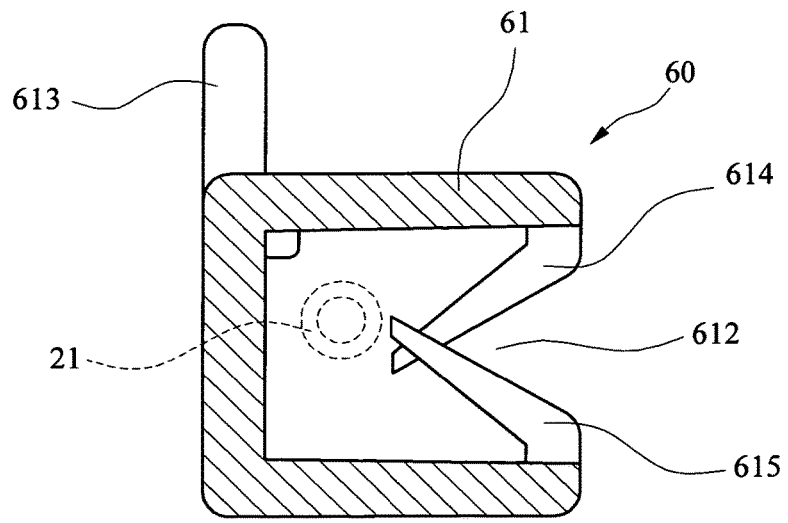
FIG. 24 is a longitudinal sectional view of the safety device shown in FIG. 23.

Referring to FIGS. 21 and 22, a blood collection apparatus incorporating a third preferred embodiment of a safety device 60 in accordance with the invention is shown. The characteristics of the third preferred embodiment are substantially the same as the first preferred embodiment and are described below.

The butterfly needle assembly 20A includes a retaining ring 27A tightly put on the needle housing 22A. A pivot 26A is formed on an outer surface of the retaining ring 27A and is pivotably disposed through the through hole 611 so that the safety device 60 can pivot about the pivot 26A (i.e., the butterfly needle assembly 20A). The third preferred embodiment has the same benefits as the first preferred embodiment.

Figure 25:
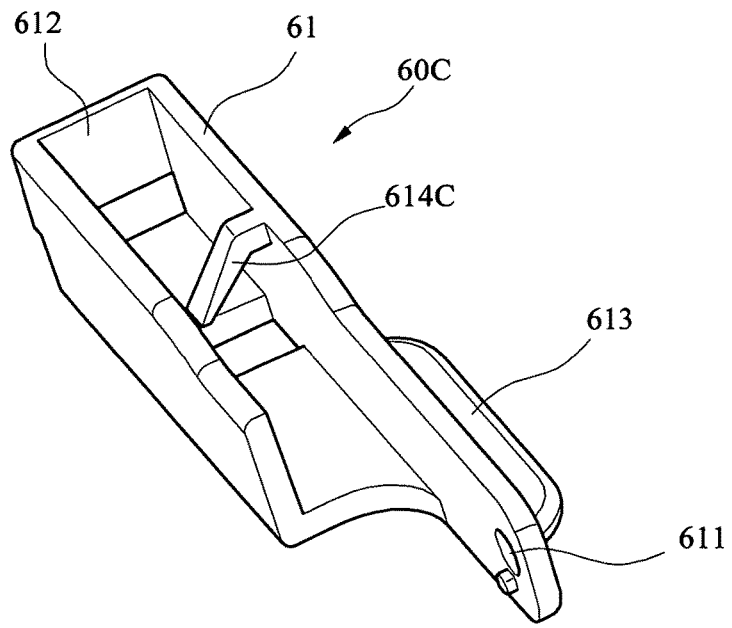
FIG. 25 is a perspective view of a safety device according to a fourth preferred embodiment of the invention.
Figure 26:
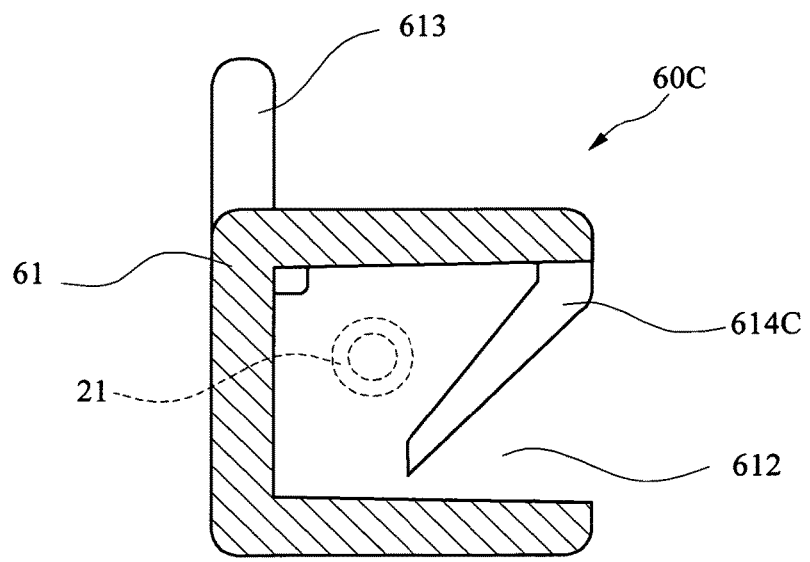
FIG. 26 is a longitudinal sectional view of the safety device shown in FIG. 25.

Referring to FIGS. 25 and 26, a blood collection apparatus incorporating a fourth preferred embodiment of a safety device 60C in accordance with the invention is shown. The characteristics of the fourth preferred embodiment are substantially the same as the first preferred embodiment and are described below.

The safety device 60C includes a single blocking member 614C in the internal space 612. The fourth preferred embodiment has the same benefits as the first preferred embodiment.

Referring to FIGS. 27 to 31, a blood collection apparatus incorporating a fifth preferred embodiment of a safety device 60D in accordance with the invention is shown. The characteristics of the fifth preferred embodiment are substantially the same as the first preferred embodiment and are described below.

The butterfly needle assembly 20D includes a needle housing 22D with the forward needle 21 mounted thereto. A tunnel 241D is interconnected two opposite wings 24D to allow a forward end of the tubing member 23 to dispose therein and secure to the needle housing 22D. The butterfly needle assembly 20D includes a retaining ring 27D tightly put on the needle housing 22D. A pivot 26D is formed on an outer surface of the retaining ring 27D and is pivotably disposed through the through hole 611D so that the safety device 60D can pivot about the pivot 26D (i.e., the butterfly needle assembly 20D). Further, two spaced first and second protuberances 616D, 617D are formed on the mouth of the through hole 611D. A peg 263D is formed on an outer surface of a stem portion of the pivot 26D below the head. The peg 263D is on the same plane as the first and second protuberances 616D, 617D.

Figure 27:
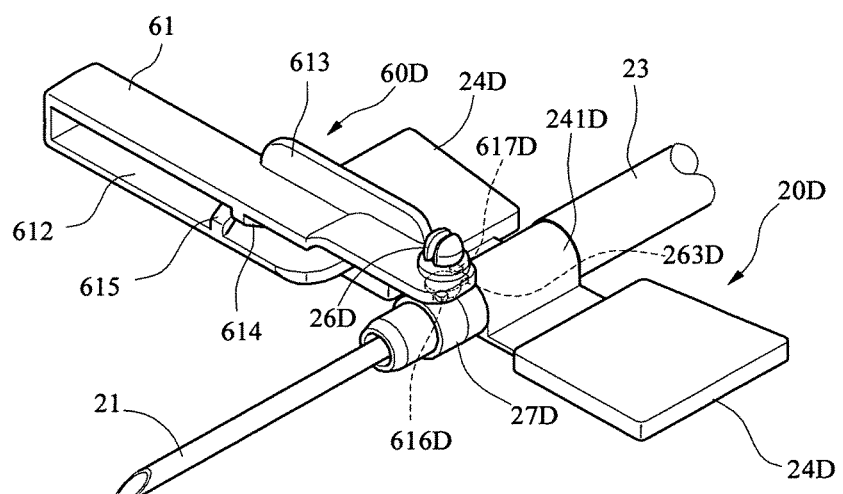
FIG. 27 is a perspective view of a safety device and a butterfly needle assembly according to a fifth preferred embodiment of the invention.
Figure 28:
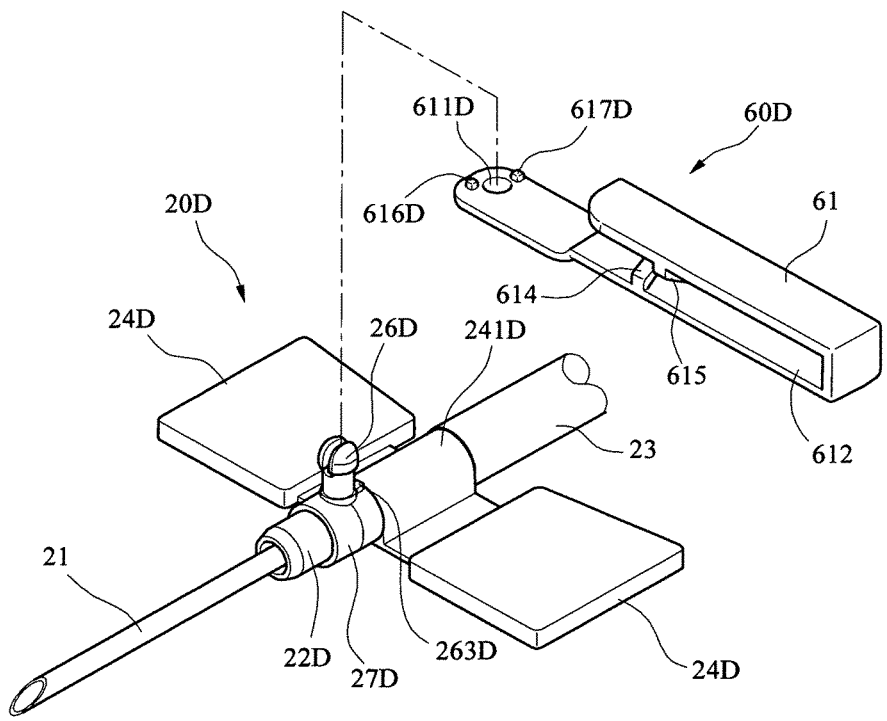
FIG. 28 is an exploded view of the safety device and the butterfly needle assembly shown in FIG. 27.
Figure 29:
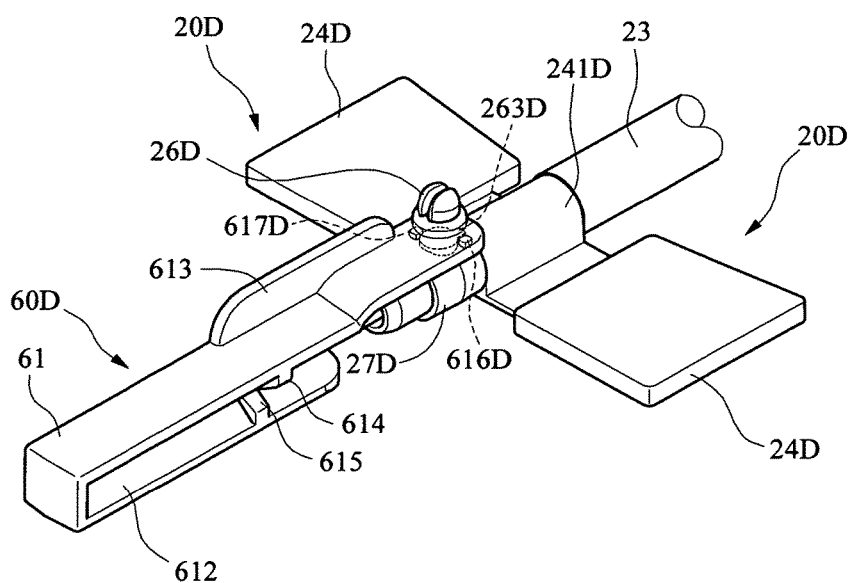
FIG. 29 is a view similar to FIG. 27 showing a use position of the safety device and the butterfly needle assembly.
Figure 30:
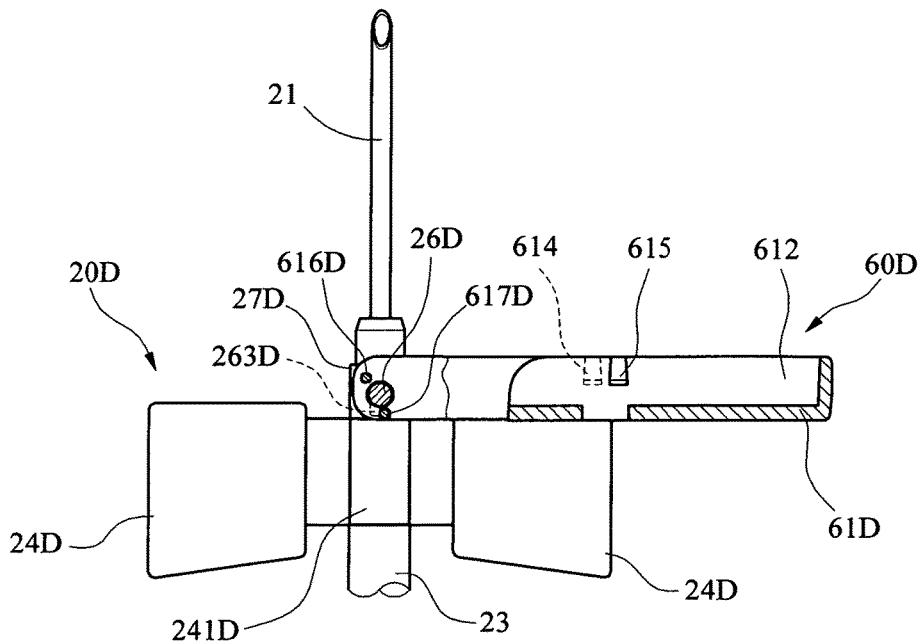
FIG. 30 is a top view in part section of the safety device and the butterfly needle assembly in a ready to use position.
Figure 31:
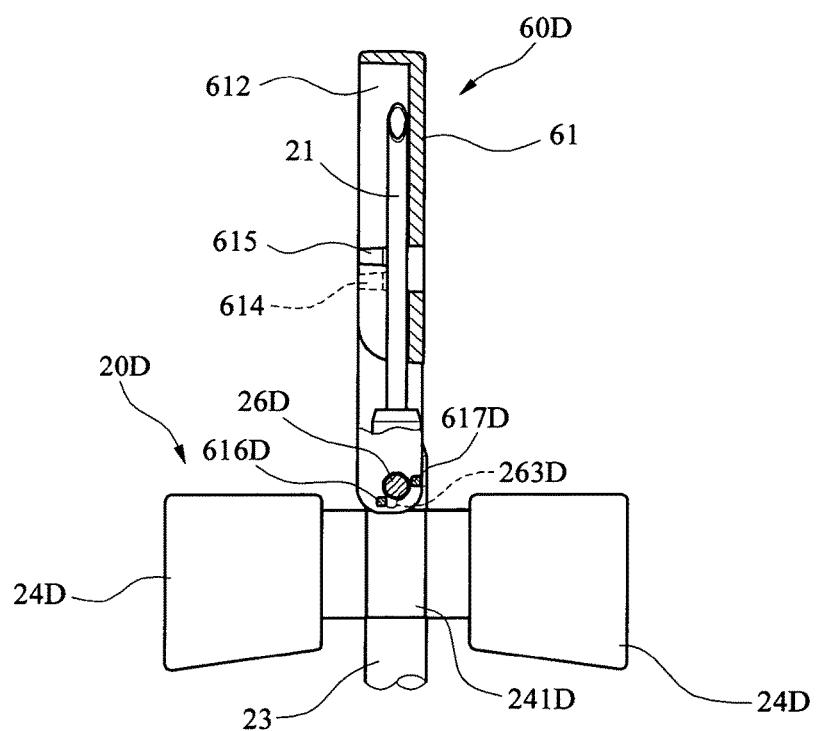
FIG. 31 is a view similar to FIG. 30 showing a use position of the safety device and the butterfly needle assembly.

Before the blood collection operation, the peg 263D is engaged with the second protuberance 617D (see FIGS. 27 and 30). After the blood collection operation, a medical employee may pivot the safety device 60D about the pivot 26D until the peg 263D is stopped by the first protuberance 616D (see FIGS. 29 and 31).

Referring to FIGS. 32 to 37, a blood collection apparatus incorporating a sixth preferred embodiment of a safety device 60E in accordance with the invention is shown. The characteristics of the sixth preferred embodiment are substantially the same as the second preferred embodiment and the butterfly needle assembly 20D of the fifth preferred embodiment is used. The characteristics of the sixth preferred embodiment are described below.

A tunnel 241D is interconnected two opposite wings 24D to allow a forward end of the tubing member 23 to dispose therein. The butterfly needle assembly 20D includes a retaining ring 27D tightly put on the needle housing. A pivot 26D is formed on an outer surface of the retaining ring 27D and is pivotably disposed through the through hole 611E so that the safety device 60E can pivot about the pivot 26D. Further, a protrusion 613A is formed on a top of the body 61A of the safety device 60E for facilitating pivotal movement of the safety device 60E by hand. Furthermore, two spaced first and second protuberances 616E, 617E are formed on the mouth of the through hole 611E. A peg 263D is formed on an outer surface of a stem portion of the pivot 26D below the head. The peg 263D is on the same plane as the first and second protuberances 616E, 617E.

Figure 32:
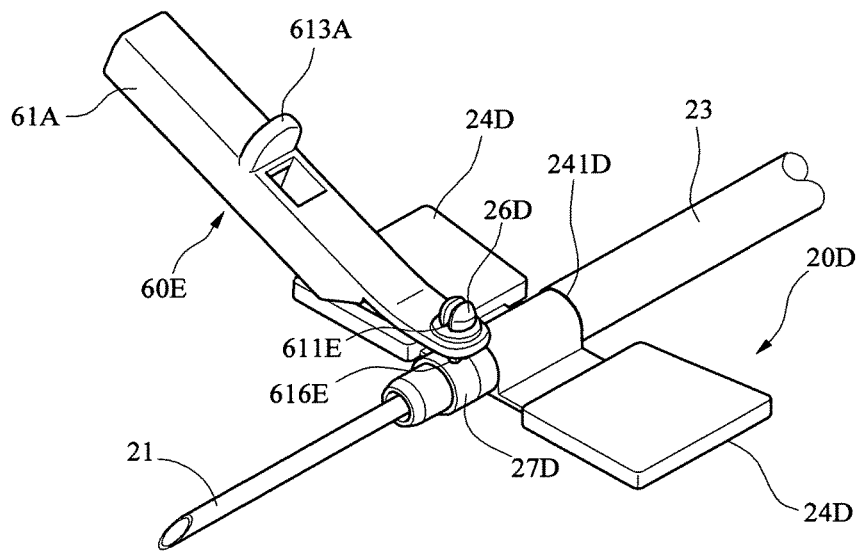
FIG. 32 is a perspective view of a safety device and a butterfly needle assembly according to a sixth preferred embodiment of the invention in a ready to use position.
Figure 33:
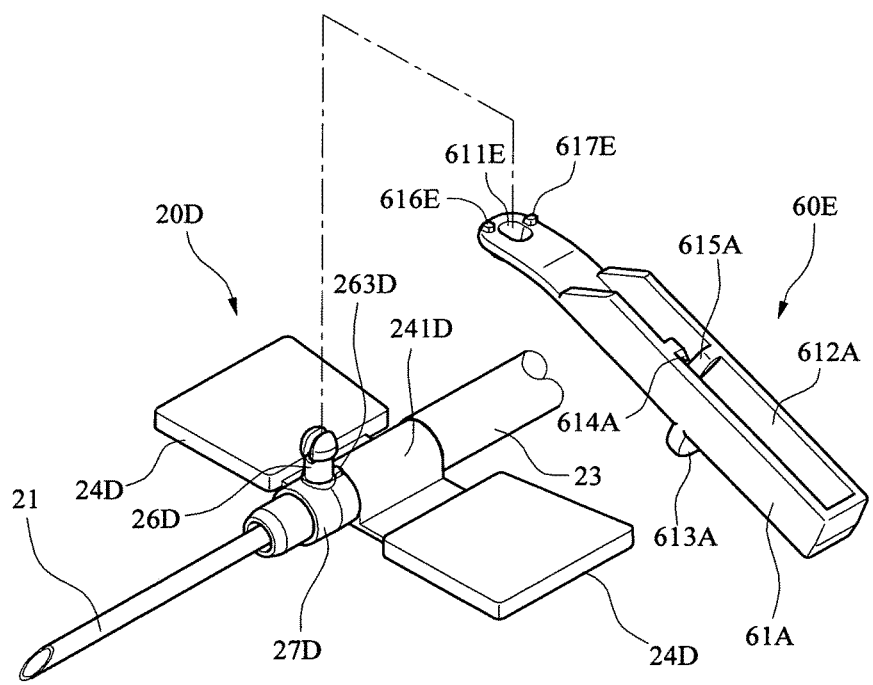
FIG. 33 is an exploded perspective view of the safety device and the butterfly needle assembly shown in FIG. 32.
Figure 34:
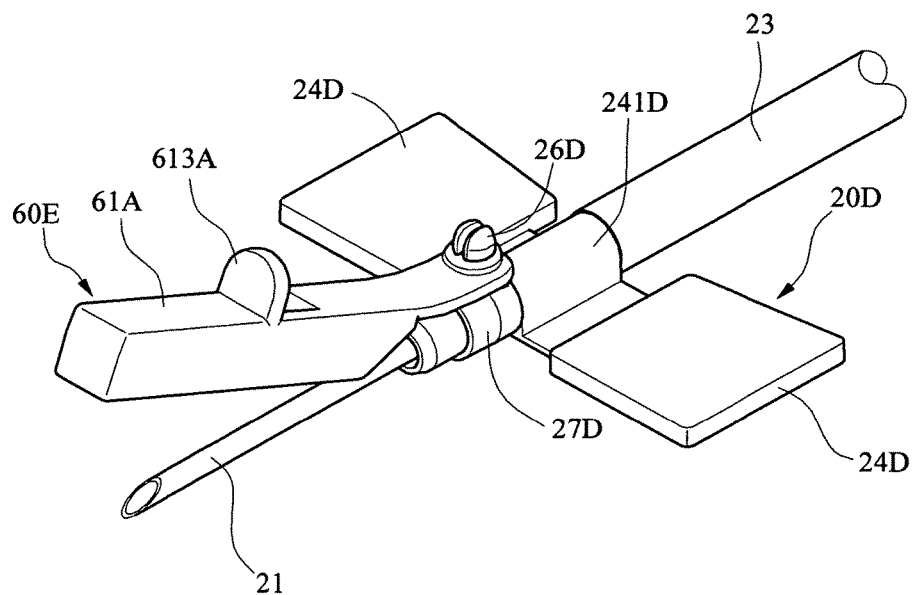
FIG. 34 is a view similar to FIG. 32 showing a position ready to use of the safety device and the butterfly needle assembly.
Figure 35:
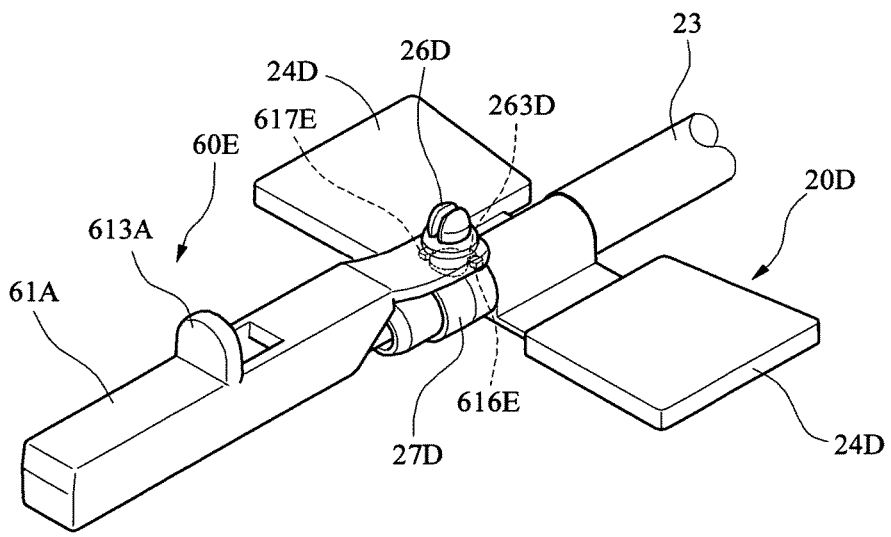
FIG. 35 is a view similar to FIG. 34 showing a use position of the safety device and the butterfly needle assembly.
Figure 36:
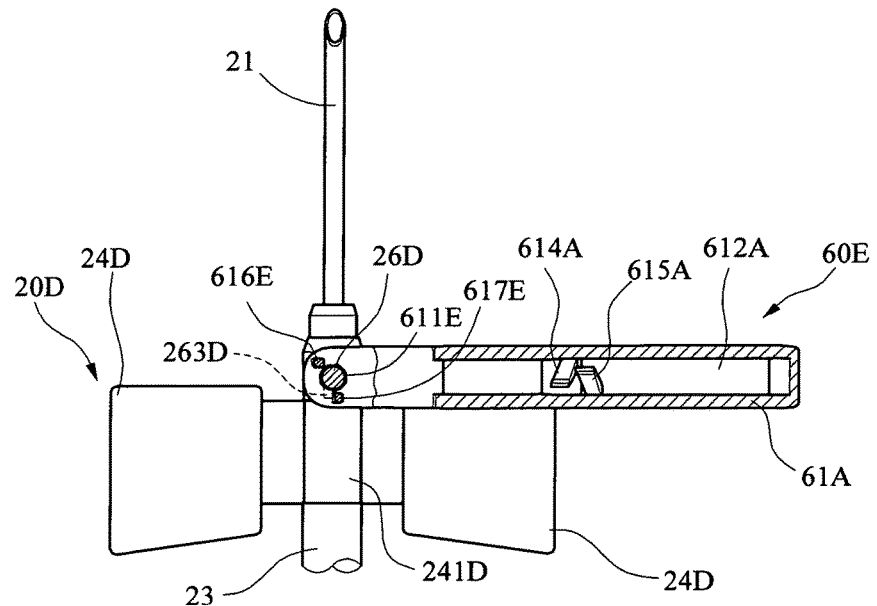
FIG. 36 is a top view of the safety device and the butterfly needle assembly of FIG. 32 in a position ready to use.
Figure 37:
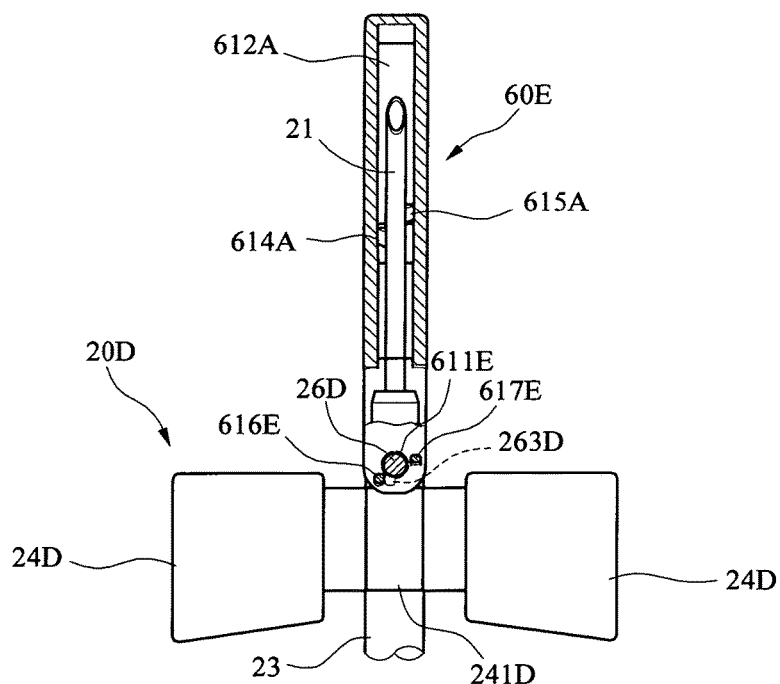
FIG. 37 is a view similar to FIG. 36 showing the safety device and the butterfly needle assembly in a use position.

Before the blood collection operation, the peg 263D is engaged with the second protuberance 617E (see FIGS. 32 and 36). After the blood collection operation, a medical employee may pivot the safety device 60D about the pivot 26D about 90 degrees by holding and pivoting the protrusion 613A to cause the needle 21 to pass through a gap between the first blocking member 614A and the second blocking member 615A to be lockingly concealed in the internal space 612A until the peg 263D is stopped by the first protuberance 616E (see FIGS. 34, 35 and 37).

While the invention has been described in terms of preferred embodiments, those skilled in the art will recognize that the invention can be practiced with modifications within the spirit and scope of the appended claims.

What is claimed is:

1. A blood collection apparatus (100) comprising:
   a blood collection assembly (10) comprising:
      a casing tube (11) including a forward nose (12), a plurality of connectors (111-115) and a rear flange (13) having a flexible projection (131); and
      a plunger (30) slidably disposed into the casing tube (11) and comprising a forward plug (31) and an elongated arm (32) including a plurality of cavities (321-325);
   a plurality of blood collection tubes (501-505);
   a plurality of adapter assemblies (40) each including a tube body (41), a first tube (411-415) extending out of one end of the tube body (41) to insert into one of the connectors (111-115) of the casing tube (11), and a second tube (421) extending out of another end of the tube body (41) to insert into one of the blood collection tubes (501-505); and
   a butterfly needle assembly (20) mounted to the nose (12) of the casing tube (11);
   wherein in a blood collection operation of pulling of the plunger (30) moves the plug (31) rearward and pivots the projection (131) to engage in one of the cavities (321-325) of the elongated arm (32) and an orifice (101-105) of each said related connector (111-115) is not blocked by the plug (31) so as to flow blood from the casing tube (11) to one of the blood collection tubes (501-505) via one of the connectors (111-115) and one of the adapter assemblies (40).

2. The blood collection apparatus of claim 1, wherein the butterfly needle assembly (20) comprises two wings (24) and a tunnel (241) interconnecting the wings (24).

3. The blood collection apparatus of claim 2, wherein the butterfly needle assembly (20) further comprises a needle housing (22), a forward needle (21) mounted to the needle housing (22), a tubing member (23) having a forward end fastened in the needle housing (22), and a housing member (25) mounted to a rear end of the tubing member (23).

4. The blood collection apparatus of claim 3, wherein the butterfly needle assembly (20) further comprises a projecting pivot member (26) formed on the needle housing (22), and a safety device (60) includes an internally hollowed body (61) having a through hole (611) at one end, the through hole (611) is pivotably put on the pivot member (26) so that the safety device (60) is configured to pivot about the pivot member (26).

5. The blood collection apparatus of claim 2, wherein the butterfly needle assembly (20) further comprises a needle housing (22) integrally formed with the tunnel (241).

6. The blood collection apparatus of claim 1, wherein the butterfly needle assembly (20) further comprises a needle housing (22), a forward needle (21) mounted to the needle housing (22), a tubing member (23) having a forward end fastened in the needle housing (22), and a housing member (25) mounted to a rear end of the tubing member (23).

7. The blood collection apparatus of claim 6, wherein the butterfly needle assembly (20) further comprises a projecting pivot member (26) formed on the needle housing (22), and a safety device (60) includes an internally hollowed body (61) having a through hole (611) at one end, the through hole (611) is pivotably put on the pivot member (26) so that the safety device (60) is configured to pivot about the pivot member (261.

8. The blood collection apparatus of claim 7, wherein the safety device (60, 60D) further comprises an internal space (612) defined by the internally hollowed body (61) and open to one side, and at least one blocking member (614, 615) disposed in the internal space (612) wherein after the blood collection operation, a pivotal movement (26, 26D) of the safety device (60, 60D) about the pivot member (26, 26D) passes the needle (21) through both one side of the internal space (612) and the at least one blocking member (614, 615) to be lockingly concealed in the internal space (612).

9. The blood collection apparatus of claim 8, wherein the safety device (60D) further comprises a spaced first and second protuberances (616D, 617D) formed proximate to the through hole (611D), wherein the pivot member (26D) comprises a peg (263D) formed on an outer surface, and wherein before the blood collection operation, the peg (263D) engages the second protuberance (617D), and after the blood collection operation, the peg (263D) is stopped by the first protuberance (616D).

10. The blood collection apparatus of claim 7, wherein the safety device (60A, 60E) further comprises an internal space (612A) defined by the internally hollowed body (61A) and open to a bottom, and at least one blocking member (614A, 615A) disposed in the internal space (612A) wherein after the blood collection operation, a pivotal movement of the safety device (60A, 60E) about the pivot member (26, 26D) passes the needle (21) through both the bottom of the internal space (612A) and the at least one blocking member (614A, 615A) to be lockingly concealed in the internal space (612A).

11. The blood collection apparatus of claim 10, wherein the safety device (60E) further comprises a spaced first and second protuberances (616E, 617E) formed proximate to the through hole (611E), wherein the pivot member (26D) comprises a peg (263D) formed on an outer surface, and wherein before the blood collection operation, the peg (263D) engages the second protuberance (617E), and after the blood collection operation, the peg (263D) is stopped by the first protuberance (616E).

12. The blood collection apparatus of claim 6, wherein the butterfly needle assembly (20A, 20D) further comprises a retaining ring (27A, 27D) securely put on the needle housing (22A, 22D), and a projecting pivot member (26A, 26D) formed on the retaining ring (27A, 27D), a safety device (60, 60D, 60E) includes an internally hollowed body (61, 61A) having a through hole (611, 611D, 611E), wherein the through hole (611, 611D, 611E) is pivotably put on the pivot member (26A, 26D) so that the safety device (60, 60D, 60E) is configured to pivot about the pivot member (26A, 26D).

13. The blood collection apparatus of claim 12, wherein the safety device (60D, 60E) further comprises a spaced first and second protuberances (616D, 616E, 617D, 617E) formed proximate to the through hole (611D, 611E), wherein the pivot member (26D) comprises a peg (263D) formed on an outer surface, and wherein before the blood collection operation, the peg (263D) engages the second protuberance (617D, 617E), and after the blood collection operation, the peg (263D) is stopped by the first protuberance (616D 616E).

14. The blood collection apparatus of claim 1, wherein the nose (12) is formed on a forward end of the casing tube (11) and is inserted into a rear housing member (25) of a tubing member (23).

15. The blood collection apparatus of claim 1, wherein the flexible projection (131) of the rear flange (13) is configured to engage within one of the cavities (321-325) on the elongated arm (32).

* * * * *